United States Patent
Lindenthaler et al.

(10) Patent No.: US 9,186,503 B2
(45) Date of Patent: *Nov. 17, 2015

(54) ADAPTIVE AIRWAY TREATMENT OF DORSAL DISPLACEMENT DISORDERS IN HORSES

(71) Applicants: MED-EL Elektromedizinische Geraete GmbH, Innsbruck (AT); Cornell University, Ithaca, NY (US)

(72) Inventors: Werner Lindenthaler, Oberperfuss (AT); Norm G. Ducharme, Ithaca, NY (US)

(73) Assignees: MED-EL Elektromedizinische Geraete GmbH, Innsbruck (AT); Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,455

(22) Filed: Mar. 17, 2014

(65) Prior Publication Data

US 2014/0200623 A1    Jul. 17, 2014

Related U.S. Application Data

(63) Continuation of application No. 13/339,487, filed on Dec. 29, 2011, now Pat. No. 8,676,325, which is a continuation-in-part of application No. 11/962,667, filed on Dec. 21, 2007.

(60) Provisional application No. 60/871,533, filed on Dec. 22, 2006.

(51) Int. Cl.
*A61N 1/36*    (2006.01)
*A61D 99/00*    (2006.01)

(Continued)

(52) U.S. Cl.
CPC .............. *A61N 1/3601* (2013.01); *A61D 99/00* (2013.01); *A61N 1/0553* (2013.01);
(Continued)

(58) Field of Classification Search
CPC . A61N 1/3601; A61N 1/3611; A61N 1/0517; A61N 1/0519
USPC .......................................................... 607/42
See application file for complete search history.

(56) References Cited

U.S. PATENT DOCUMENTS

| 4,830,008 A | 5/1989 | Meer .......................... 128/421 |
| 4,887,593 A | 12/1989 | Wiley et al. ................... 606/45 |

(Continued)

FOREIGN PATENT DOCUMENTS

| JP | 11514557 | 12/1999 | ............... A61N 1/36 |
| WO | WO 97/49455 | 12/1997 | ............... A61N 1/36 |

OTHER PUBLICATIONS

Aviv et al., "Overcoming Laryngospasm by Electrical Stimulation of the Posterior Cricoarytenoid Muscle," Otolaryngol Head and Neck Surgery 1989, vol. 100, pp. 110-118.

(Continued)

*Primary Examiner* — Eric D. Bertram
(74) *Attorney, Agent, or Firm* — Sunstein Kann Murphy & Timbers LLP

(57) ABSTRACT

A method of using an airway treatment system for treating a dorsal displacement disorder in a horse includes detecting an elevated activity level of the horse using one or more treatment sensors, generating a treatment signal based on the detected elevated activity level, using a pacemaker processor, to strengthen one or more muscles involved in displacing a laryngeal anatomical structure relative to an airway of the horse, and using one or more stimulation electrodes, configured to interface with tissue of the horse, to deliver the treatment signal to the tissue of the horse to maintain an unobstructed airway.

18 Claims, 8 Drawing Sheets

(51) Int. Cl.
 *A61N 1/05* (2006.01)
 *A61N 1/372* (2006.01)
(52) U.S. Cl.
 CPC ........... *A61N 1/0556* (2013.01); *A61N 1/0558* (2013.01); *A61N 1/0502* (2013.01); *A61N 1/36139* (2013.01); *A61N 1/37282* (2013.01)

(56) References Cited

U.S. PATENT DOCUMENTS

| | | | |
|---|---|---|---|
| 5,016,647 A | 5/1991 | Sanders | 128/787 |
| 5,111,814 A | 5/1992 | Goldfarb | 128/419 |
| 5,211,173 A | 5/1993 | Kallok et al. | 128/419 |
| 5,897,579 A | 4/1999 | Sanders | 607/42 |
| 6,021,352 A | 2/2000 | Christopherson et al. | 607/42 |
| 6,659,960 B2 * | 12/2003 | Derksen et al. | 600/529 |
| 6,978,787 B1 | 12/2005 | Broniatowski | 128/898 |
| 7,069,082 B2 | 6/2006 | Lindenthaler | 607/41 |
| 7,175,645 B1 | 2/2007 | Blach et al. | 606/199 |
| 8,136,532 B2 | 3/2012 | Lindenthaler et al. | 128/898 |
| 8,676,325 B2 * | 3/2014 | Lindenthaler et al. | 607/42 |
| 2002/0156507 A1 | 10/2002 | Lindenthaler | 607/17 |
| 2003/0093128 A1 | 5/2003 | Freed et al. | 607/42 |
| 2004/0215290 A1 | 10/2004 | Zealear | 607/50 |
| 2005/0085753 A1 | 4/2005 | Ducharme et al. | 602/17 |
| 2006/0178703 A1 | 8/2006 | Huston et al. | 607/2 |
| 2006/0247729 A1 | 11/2006 | Tehrani et al. | 607/42 |
| 2006/0282127 A1 * | 12/2006 | Zealear | 607/42 |
| 2007/0282317 A1 | 12/2007 | Lindenthaler | 607/32 |
| 2008/0071231 A1 | 3/2008 | Lindenthaler | 604/272 |

OTHER PUBLICATIONS

Bergman et al., "Respiratory Rhythmically Regulated Electrical Stimulation of paralyzed Muscles," Laryngoscope, 1984, pp. 1376-1380.
Bergmann et al., "Long-Term Implantation of a System of Electrical Stimulation of Paralyzed Laryngeal Muscles in Dogs," Laryngoscope 98, Mar. 1988, pp. 455-459.
Bergmann, "Functional Disorders of the Superior Laryngeal Nerve in Patients Suffering from Laryngeal Nerve Palsies," HNO-Praxis 11, 1986, pp. 153-159.
Bergmann et al., "Chronic Implantation of a System for Electrical Stimulation of Paralyzed Laryngeal Muscles in Dogs," HNO-Praxis 11, 1986, pp. 231-239.
Bergmann, "Indication and Limits of the Significance of EMG Recording from Larynx Muscles," HNO-Praxis 11, 1986, pp. 83-88.
Bergmann et al., "Histochemical Characteristics of the Normal and Paretic Dog Laryngeal Muscle," HNO-Praxis 12, 1987, pp. 259-266.
Billante et al., "Effect of Chronic Electrical Stimulation of Laryngeal Muscle on Voice," Ann Otol Rhinol Laryngol, 111(4), Apr. 2002, pp. 328-332.
Broniatowski et al., "Laryngeal Pacemakers: Electronic Pacing of Reinnervated Posterior Cricoarytenoid Muscles in the Canine," Laryngoscope, 95, Oct. 1985, pp. 1194-1198.
Broniatowski et al., "The Future of Electronic Pacing in Laryngeal Rehabilitation," Am. J. Otolaryngol, 11(1), Jan.-Feb. 1990, pp. 51-62.
Broniatowski et al., "The Role of Artificial Organs in Restoration of Laryngeal Function," Trans ASAIO Apr.-Jun. 1990, vol. 36(2), pp. 47-49.
Broniatowski et al., "Electronic Control of Laryngeal Spasm in Blockage of Orthodromically Induced Action Potentials in Intact Canine Recurrent Laryngeal Nerves," Laryngoscope, 100(8), Aug. 1990 pp. 892-895.
Broniatowski et al. "Selective Feedback Control of Spastic Musculature in a Canine Model," ASAIO Journal, 38(3), Jul.-Sep. 1992, pp. M248-M252.
Broniatowski et al., "Electronic Pacing of Incapacitated Head and Neck Structures," Trans. ASAIO 1991, vol. 37, pp. 553-558.
Broniatowski et al., "Electronic Control of Pathologic Tone Disturbances in the Larynx," ASAIO Journal, Jan.-Mar. 1993, vol. 39(1), pp. 24-28.
Broniatowski et al., "Dynamic Control of the Larynx and Future Perspectives in the Management of Deglutitive Aspiration," Dysphagia, vol. 8(4), Fall 1993, pp. 334-336.
Broniatowski et al., "An Experimental Model for Complex Dynamic Control of the Reinnervated Face," Eur Arch Otorhinolaryngology, 1994, pp. S147-S148.
Broniatowski et al., "Electronic Integration of Glottic Closure and Ciropharyngeal Relaxation for the Control of Aspiration: A Canine Study," Otolaryngology Head Neck Surgery, Mar. 1995, vol. 112(3), pp. 424-429.
Broniatowski et al., "Long-Term Excitability and Fine Tuning of Nerve Pedicles Reinnervating Strap Muscle in the Dog," Ann Otol Rhinol Laryngol, 107(4), 1998, pp. 301-311.
Broniatowski et al., "Current Evaluation and Treatment of Patients with Swallowing Disorders," Otolaryngology Head Neck Surgery, Apr. 1999, vol. 120, No. 4, pp. 464-473.
Broniatowski et al., "Vagal Stimulation for Reciprocal Coupling Between Glottic and Upper Esophageal Sphincter Activities in the Canine," Dysphagia, 14(4), Fall 1999, pp. 196-203.
Broniatowski et al., "Electronic Analysis of Intrinsic Laryngeal Muscles in Canine Sound Production," Ann Otol Rhinol Laryngol, 111(6), Jun. 2002, pp. 542-552.
Diamond et al., "The Intramuscular Nerve Supply of the Posterior Cricoarytenoid Muscle of the Dog," Laryngoscope, vol. 102(3), Mar. 1992, pp. 272-276.
Herrmann et al., "Long-term experimental Electrostimulation of Denervated Laryngeal Muscle in Dogs," Zentralbl. allg. Pathol. 133(4), 1987, pp. 337-350.
Herzon et al., "New Laser Ruler Instrument for Making Measurements Through an Endoscope," Otolaryngology Head and Neck Surgery, Jun. 1997, 116, pp. 689-692.
Hillel et al., "Evaluation and Management of Bilateral Vocal Cord Immobility," Otolaryngology Head and Neck Surgery, Dec. 1999, vol. 121(6), pp. 760-765.
Hoffmann et al., "New Technologies in Manufacturing of Different Implantable Microelectrodes as an Interface to the Peripheral Nervous System," Biomedical Robotics and Biomechatronics, Feb. 20-22, 2006, pp. 414-419.
Holcombe et al., "Electromyographic activity of the hyoepiglotticus muscle and control of epiglottis position in horses," American Journal of Veterinary Research, vol. 63, No. 12, pp. 1617-1621, Dec. 2002.
Katada et al., "Functional Electrical Stimulation of Laryngeal Adductor Muscle Restores Mobility of Vocal Fold and Improves Voice Sounds in Cats with Unilateral Laryngeal Paralysis," Neuroscience Research, 50(2), Oct. 2004, pp. 153-159.
Kojima et al., "Laryngeal Pacing in Unilateral Vocal Cord Paralysis, an Experimental Study," Arch Otolaryngology Head Neck Surgery, Jan. 1990, vol. 116(1), pp. 74-78.
Kojima et al., "Electrical Pacing for Dynamic Treatment of Unilateral Vocal Cord Paralysis, Experiment in Long-Denervated Muscle," Ann Otol Rhinol Laryngol, 100(1), Jan. 1991, pp. 15-18.
Kraus et al., "Laryngeal Electrode Platform: An Indwelling Device for Mobilizing the Vocal Cords," Ann Otol Rhinol Laryngol, 96(6), Nov.-Dec. 1987, pp. 674-679.
Lanmüller et al., "Battery-Powered Implantable Nerve the Stimulator for Chronic Activation of Two Skeletal Muscles Using Multichannel Techniques," Artificial Organs, vol. 23, No. 5, May 1999, pp. 399-402.
Lanmüller et al., "Long-Term Electromyogram Recording from the Posterior Cricoarytenoid Muscle as a Potential Biological Trigger for Phrenic Pacing: Results of an Animal Study," Artificial Organs, Sep. 1999, vol. 23, No. 9, pp. 860-868.
Luger et al., "Diaphragm EMG as a Control Signal for Fes of the Denervated Posticus Muscle," Biomedical Engineering and Physics, AKH-04L, Wahringer Gurtel 18-20, A-1090, Vienna, Austria, pp. 136-139.

(56) References Cited

OTHER PUBLICATIONS

Martin et al., "Electrodiagnostic and Histometric Investigations of the Influence of Electric Stimulation on the Atrophy of Denervated Laryngeal Muscles in Animal Experiments," Laryng. Rhinol. Otol. 62, 1983, pp. 590-596.

Mayr et al., "Basic Design and Construction of the Vienna FES Implants; Existing Solutions and Prospects for New Generations of Implants," Medical Engineering & Physics, 23(1), Jan. 2001, pp. 53-60.

Mu et al., "The Sensory Nerve Supply of the Human Oro- and Laryngopharynx: A Preliminary Study," The Anatomical Record, vol. 258(4), Apr. 2000, pp. 406-420.

Otto et al., "Coordinated Electrical Pacing of Vocal Cord Abductors in Recurrent Laryngeal Nerve Paralysis," Otolaryngol Head and Neck Surgery, vol. 93, No. 5, Oct. 1985, pp. 634-638.

Otto et al., "Sensitivity and Specificity of Intraoperative Recurrent Laryngeal Nerve Stimulation in Predicting Postoperative Nerve Paralysis," Ann Otol Rhinol Laryngol, 111(11), Nov. 2002, pp. 1005-1007.

Sanders et al., "Transcutaneous Electrical Stimulation of the Recurrent Laryngeal Nerve: A Method of Controlling Vocal cord Position," Otolaryngology Head and Neck Surgery, vol. 95(2), Sep. 1986, pp. 152-157.

Sanders et al., "Transcutaneous Electrical Stimulation of the Recurrent Laryngeal Nerve in Monkeys," Ann Otol Rhinol Laryngol, vol. 96, Jan.-Feb. 1987, pp. 38-42.

Sanders et al., "Transtracheal/Transesophageal Stimulation of the Recurrent Laryngeal Nerve," Laryngoscope, 97(6), Jun. 1987, pp. 663-667.

Sanders et al., "Transmucosal Electrical Stimulation of Laryngeal Muscles," Ann Otol Rhinol Laryngol, vol. 98, May 1989, pp. 339-345.

Sanders et al., "Electrical Stimulation of Laryngeal Muscle," Otolaryngol Clinics of North America, vol. 24, No. 5, Oct. 1991, pp. 1253-1274.

Sanders et al., "The Three Bellies of the Canine Posterior Cricoarytenoid Muscle: Implications for Understanding Laryngeal Function," Laryngoscope, vol. 103(2), Feb. 1993, pp. 171-177.

Sanders et al., "Arytenoid Motion Evoked by Regional Electrical Stimulation of the Canine Posterior Cricoarytenoid Muscle," Laryngoscope, 104(4), Apr. 1994, pp. 456-462.

Sanders et al., "The Innervation of the Human Posterior Cricoarytenoid Muscle: Evidence for at Least Two Neuromuscular compartments," Laryngoscope, vol. 104(7), Jul. 1994, pp. 880-884.

Simpson et al., "Vocal Cord Paralysis: Clinical and Electrophysiologic Features," Muscle Nerve, 16(9), Sep. 1993, pp. 952-957.

Weed et al., "Reinnervation of the Allograft Larynx in the Rat Laryngeal Transplant Model," Otolaryngology Head and Neck Surgery, vol. 113, No. 5, Nov. 1995, pp. 517-529.

Widick et al., "Awake Evoked Electromyography Recording From the Chronically Implanted Rat," Laryngoscope, 104, Apr. 1994, pp. 420-425.

Zealear et al., "Control of Paralyzed Axial Muscles by Electrical Stimulation," Acta Otolaryngol, 83(5-6), May-Jun. 1977, pp. 514-527.

Zealear et al., "Technical Approach for Reanimation of the Chronically Denervated larynx by Means of Functional Electrical Stimulation," Ann Otol Rhinol Laryngol, 103, 1994, pp. 705-712.

Zealear et al., "Effects of Denervation on Posterior Cricoarytenoid Muscle Physiology and Histochemistry," Ann Otol Rhinol Laryngol, 103(10), Oct. 1994, pp. 780-788.

Zealear et al., "The Effects of Chronic Electrical Stimulation on Laryngeal Muscle Physiology and Histochemistry," ORL, Mar.-Apr. 2000, vol. 62(2), pp. 81-86.

Zealear et al., "The Effects of Chronic Electrical Stimulation on Laryngeal Muscle Reinnervation," ORL, Mar.-Apr. 2000, vol. 62(2), pp. 87-95.

Zealear et al., "Determination of the Optimal Conditions for Laryngeal Pacing with the Itrel II Implantable the Stimulator," Otolaryngology Head Neck Surgery, Sep. 2001, vol. 125, No. 3, pp. 183-192.

Zealear et al., "The Biocompatibility, Integrity and Positional Stability of an Injectable Microstimulator for Reanimation of the Paralyzed Larynx," IEEE Transactions on Biomedical Engineering, vol. 48, No. 8, Aug. 2001, pp. 890-897.

Zealear et al., "Electrical Stimulation of a Denervated Muscle Promotes Selective Reinnervation by Native Over Foreign Motoneurons," J. Neurophysiology, 87(4), Apr. 2002, pp. 2195-2199.

Zealear et al., "Electrically Stimulated Glottal Opening Combined with Adductor Muscle Botox Blockade Restores Both Ventilation and Voice in a Patient with Bilateral Laryngeal Paralysis," Ann Otol Rhinol Laryngol, 111(6), Jun. 2002, pp. 500-506.

Zealear et al., "Neurophysiology of Vocal Fold Paralysis," Otolaryngol Clinics North America, 37(1), Feb. 2004, pp. 1-23.

Zealear et al., "Evoked Electromyographic Technique for Quantitative Assessment of the Innervation Status of Laryngeal Muscles," Ann Otol Rhinol Laryngol 114(7), Jul. 2005, pp. 563-572.

Zealear et al., "Reanimation of the Paralyzed Human Larynx with an Implantable Electrical Stimulation Device," Laryngoscope, 113, Jul 2003, pp. 1149-1156.

Zealear et al., "Electrical Pacing of the Paralyzed Human Larynx," Ann Otol Rhino Laryngol, 105(9), Sep. 1996, pp. 689-693.

Zrunek et al., "Laryngeal Pacemaker: Activity of the Posterior Cricoarytenoid Muscle (PCM) and the Diaphragm During Respiration in Sheep," Acta Otolaryngol, Sep.-Oct. 1989, vol. 108(3-4), pp. 311-316.

Zrunek et al., "A Laryngeal Pacemaker for Inspiration-Controlled, Direct Electrical Stimulation of the Denervated Posterior Cricoarytenoid Muscle in Sheep," Eur Arch Otorhinolaryngology, 248(8), 1991, pp. 445-448.

European Patent Office, Supplementary European Search Report—Application No. 07871728 dated Nov. 5, 2012, 9 pages.

\* cited by examiner

Effect of muscle stimulation on three laryngeal points
- assessed radiographically

ADAPTIVE AIRWAY TREATMENT OF DORSAL DISPLACEMENT DISORDERS IN HORSES

This application is a Continuation of U.S. patent application Ser. No. 13/339,487 filed Dec. 29, 2011, now U.S. Pat. No. 8,676,325, which is a Continuation-in-Part of U.S. patent application Ser. No. 11/962,667 filed Dec. 21, 2007, which in turn claims priority from U.S. Provisional Patent Application 60/871,533, filed Dec. 22, 2006, the contents of which are incorporated herein by reference in their entirety.

TECHNICAL FIELD

This application relates to relieving airway impairments in horses, specifically disorders associated with dorsal displacement of the soft palate.

BACKGROUND ART

FIG. 1 shows various anatomical structures associated with the head of a horse. Among these, the airway structures, and in particular the larynx and pharynx, are susceptible to various disorders which affect the horse's health and its ability to perform normally. The larynx is innervated by the recurrent laryngeal nerves (RLN) which contain motor fibers that innervate both the abductor/opener and adductor/closer muscles of the arytenoid cartilages and their associated vocal folds. The soft palate normally fits closely around the ventral border of the epiglottis.

Airway impairment produces two symptoms, abnormal sounds and/or poor performance. Abnormal sounds are detected by the human ear (riders, judges) and can be quantitate by time-frequency spectrogram. Horses produce inspiratory sounds characterized by three frequency bands centered at approximately 0.3, 1.6, and 3.8 k Hz; See Derksen F J et al., *Spectrum Analysis Of Respiratory Sounds In Exercising Horses With Experimentally Induced Laryngeal Hemiplegia Or Dorsal Displacement Of The Soft Palate*, Am J Vet Res. 2001 May; 62 (5):659-64, incorporated herein by reference. Respiratory sounds of horses have been recorded using a radiostethoscope such as that disclosed by Attenburrow et al., *Resonant Frequency of the Lateral Ventrical and Saccule and Whistling*, Equine Exercise Physiology, pp 27-32, and in U.S. Pat. No. 4,218,584 to Attenburrow, both of which describe a stethoscope for detecting and recording data from a horse while the horse is walking, trotting, cantering, jumping, and galloping. A transducer such as a microphone is attached to the animal's skin adjacent to the windpipe. The electrical output from the transducer is transferred to a radio transmitter mounted on the animal or its harness. The radio transmitter can transmit signals a distance from the horse to allow for monitoring the horse's breathing from a distance. U.S. Pat. No. 6,228,037 describes a method and apparatus for recording and analysis of respiratory sounds in exercising horse, and U.S. Pat. No. 6,659,960 describes a method and system for continuous monitoring and diagnosis of body sounds, which discloses a portable unit for recording the upper airway respiratory sounds of an exercising horse to determine whether the horse suffers from an upper airway obstruction condition.

Some horses exhibit a disorder of the upper airway known as dorsal displacement of the soft palate (DDSP). Pulmonary ventilation at rest is adequate, but during exercise the cross sectional area of the horse pharynx is reduced by collapse during exhalation. This results in significant airflow reduction which is generally associated with an abnormal upper respiratory noise at exercise. In horses used for competition, the decreased volume of airflow interferes with performance and may impair the horse's ability to compete. Although conventional methods of treatment have been useful in some horses, they are less than ideal since they have only modest success rates and significant complications.

The specific pathophysiology of DDSP is that during exercise horses normally interlock their soft palate and the epiglottis to form a direct open airway from the nasal cavity to the trachea. But in some horses, the soft palate displaces dorsally during exercise, the free end of the palate then lies in the airway and causes a major obstruction to expired air. The exact cause of DDSP is not known, however, it is believed to be caused by either direct mechanical displacement by posterior movements of the tongue, or weakness in the muscles of the soft palate or those that raise the epiglottis or the entire larynx.

Several muscles are related to movement of the larynx and pharynx, but the specific role of each is not well understood. US Patent Publication 2007123950 described a twelve muscle model of the pharyngeal and laryngeal airway and showed that neuromuscular stimulation of just one or two of the muscles sufficed to move the hyoid bone. Two airway muscles could be coordinated synergistically to protect the pharyngeal and laryngeal airway by a distance reduction of the hyoid complex and larynx relative to the chin. Specifically, stimulating the thyrohyoid muscle reduced the distance of the hyoid complex relative to the larynx. And geniohyoid muscle stimulation in combination with at least one other muscle also generated the synergy of simultaneous reduction of distance of the hyoid complex and the larynx relative to the chin. Multiple intramuscular electrodes were placed in two or more upper airway muscles and controlled by an implanted stimulation device.

Functional electrical stimulation ("FES") refers to the application of stimulation devices to nerves and muscles to treat medical disorders. Application of FES to paralyzed laryngeal muscles was introduced into human clinical otolaryngology in 1977 by Zealear D L, Dedo H H, *Control Of Paralyzed Axial Muscles By Electrical Stimulation*, Acta Otolaryngol (Stockholm) 1977, 83:514-27, incorporated herein by reference. The most successful FES system to date is the cardiac pacer which has become a routine part of cardiac disease therapy: Lynch, *Cardiovascular Implants*, in *Implants*, Lynch ed., Van Nostrand Rheinhold, New York 1982, incorporated herein by reference. However, there are a variety of other FES systems, of which the most heavily researched are FES systems to restore locomotion to paraplegics and arm motion to quadriplegics: Peckham, IEEE Trans. Biomed. Eng. 1991, 28: 530, incorporated herein by reference. Other motor control devices restore bladder control to paraplegics and diaphragm function to high quadriplegics: Erlandson, Scand. J. Urol. Nephrol. 44 Suppl: 31, 1978; Glenn, Ann. Surg. 183: 566, 1976, incorporated herein by reference. There also are FES devices designed to rehabilitate the sensory deficits, such as the cochlear implant: Hambrecht, Ann. Otol. Rhinol. Laryngol. 88: 729, 1979, incorporated herein by reference. To date such systems have not been developed for horses which present different clinical conditions from humans.

An FES device for the equine applications must be effective and also must conform to the rules of the governing bodies that oversee equine sports. In thoroughbred and standard breed racing, this requires that the device must not give the horse an unfair advantage. In addition, it cannot allow tampering with the horse's performance. Specifically, as wagering is an integral part of the sport, there cannot be a way of adjusting the device to manipulate the horse's performance.

SUMMARY OF THE EMBODIMENTS

Embodiments of the present invention are directed to treating a dorsal displacement disorder in a horse such as dorsal displacement of the soft palate, nasopharyngeal collapse, rostral displacement of the palatopharyngeal arch, or epiglottic retroversion. A pacemaker processor generates a dorsal displacement disorder treatment signal responsive to at least one therapy parameter for treating the dorsal displacement disorder. One or more stimulation electrodes interfaces with tissue of the horse for delivering the treatment signal to continuously or intermittently (coordination with breathing frequency) stimulate soft palate tissue of the horse during an entire period of increased activity of the horse.

The device or some portion of it may be incorporated into the racing gear of the horse. The device or some portion of it also may be implanted in the horse. Any implanted portion of the device would communicate transcutaneously or percutaneously with the portion of the device located externally to the horse. For example, transcutaneous communication may be based on at least one of electromagnetic induction, acoustic energy, optical energy, and capacitor coupling. The device or a portion of it may be temporarily placed on the skin of the horse when the device is operating to provide external signals to the implanted portion of the device. The treatment signal may be derived from at least one of an electromyogram, an electronystagmograph, an electroglottograph, an electroencephalograph, a biopotential sensor, an ultrasound sensor, a hall sensor, a microphone, a pressure sensor, a strain transducer, a mechanical deformation sensor, accelerometer and a motion sensor. The implanted portion may include a power source which is charged percutaneously or transcutaneously.

The treatment signal may be applied to the tissue of the horse based on a signal derived from a biological function of the horse. The treatment signal may be applied to the tissue of the horse using a biphasic waveform. The stimulation electrodes may be based on at least one of a cuff electrode, a multipolar cuff electrode, a tripolar cuff electrode, a flat nerve electrode, an epineural electrode, a shaft electrode, a longitudinal intrafascicular electrode, a thin wire electrode, a micro-machined electrode, and a sieve electrode, any of which may be capable of differential activation causing stimulation to a specific area of the upper airway tissue.

Specific embodiments may further include one or more sensor electrodes for sensing at least one therapy parameter related to operation of the device. The therapy parameter may specifically relate to at least one of air flow characteristics of the airway tract of a horse, contractile characteristics of the airway tissue of a horse, electrical characteristics of a portion of the body of the horse, blood gases concentration of the horse, temperature of a portion of the body of the horse, pH of a portion of the body of the horse, chemical constituency of a portion of the body of the horse, and physiological state of the horse. The sensor electrodes may be placed externally on the horse, and/or implanted in the horse. The sensor electrodes may be connected to the pacemaker by one or more leads and/or integrated into a housing containing the pacemaker processor. The treatment signal may further be a function of the one or more stimulation electrodes, or a horse expert, or some combination thereof. In specific embodiments, the sensor electrodes may be implanted in the body of the horse, and/or may include an accelerometer which detects activity level of the horse.

In other specific embodiments, the therapy parameter may relate to delivery efficiency of the treatment signal by the one or more stimulator electrodes, for example, for at least one of vocal cord function, functioning of another segment of the upper airway tissue, and some other parameter inside the horse's body. In addition or alternatively, the therapy parameter may include at least one of pressure, contractile force, airflow rate, airflow pressure, airflow amount, airflow velocity, temperature, impedance, blood gases concentration, pH, and chemical constituency. The therapy parameter may relate to horse activity level based on at least one of cardiac activity, respiratory activity, and electromyographic activity. The therapy parameter may relate to a posture or activity level of the horse, such as whether the horse is asleep or awake.

The treatment signal may be a function of a regular periodic analysis of the therapy parameter, or an irregular non-periodic analysis of the therapy parameter. The sensor electrodes may sense physiological conditions continuously or periodically. The pacemaker processor may capture the therapy parameter at selected time intervals, which may be selected to conserve a power source associated with the system. In addition or alternatively, the pacemaker processor may capture the therapy parameter in response to a user input from a user interface, for example, based on a magnetic input from the user.

Specific embodiments may also include at least one sensor electrode for sensing the at least one therapy parameter. This may include at least one of electrical stimulation, electrical bio-potentials from tissue activity evoked by stimulation, vocal fold abduction, vocal cord adduction, and airflow changes related to vocal fold position. The sensor electrode may sense vocal fold abduction by at least one of monitoring proper airflow based on at least one of airway sound, subglottic pressure, and temperature. A sensor electrode may also sense vocal fold movement based on vocal fold displacement, for example, by measurement with at least one of a laryngeal tissue strain gauge, trans-glottis light sensing, changes in laryngeal tissue impedance, and video observation of the vocal folds. The sensor electrode may sense inspiratory airflow interference such as by inspiratory airflow interference based pressure associated with at least one of the subglottis, the trachea, or extra-trachea intra-thorax. The sensor electrode may sense inefficient respiration during exercise such as by systemic physiologic signals including at least one of a decrease in blood oxygen and an increase in $CO_2$. The sensor electrode may include a radiostethoscope and/or a microphone transducer attached to the subject's skin adjacent to the windpipe. For example, an external radio transmitter may be in communication with the microphone transducer for monitoring the horse's breathing from a distance.

Embodiments of the present invention also include an airway treatment system for treating a dorsal displacement disorder in a horse. A pacemaker processor generates a dorsal displacement disorder treatment signal during an exercise period of the horse based on anterior displacement of the tongue relative to the airway. One or more stimulation electrodes delivers the treatment signal to tissue of the horse to control the anterior displacement of the tongue and maintain the airway unobstructed during the exercise period. In specific embodiments, the tissue of the horse may include geniohyoid, genioglossus, and/or mylohyoid muscle tissue, and/or hypoglossal nerve tissue.

Embodiments of the present invention also include an airway treatment system for treating a dorsal displacement disorder in a horse. A pacemaker processor generates a dorsal displacement disorder treatment signal to strengthen one or more palatal muscles of a horse susceptible to a dorsal displacement disorder. One or more stimulation electrodes delivers the treatment signal to tissue of the horse to maintain the airway unobstructed during the exercise period. The tissue of the horse may specifically include palatoglossus and/or palatopharyngeous muscle tissue, and/or hypoglossal, vagal, and/or glossalpharyngeal nerve tissue.

Embodiments of the present invention also include an airway treatment system for treating a dorsal displacement disorder in a horse. A pacemaker processor generates a dorsal displacement disorder treatment signal during an exercise period of the horse based on displacement of a laryngeal anatomical structure relative to the airway. One or more stimulation electrodes deliver the treatment signal to tissue of the horse to raise elevated and/or move rostrally the laryngeal anatomical structure and/or hyoid apparatus and maintain the airway unobstructed during the exercise period.

The laryngeal anatomical structure may specifically include the larynx and/or epiglottis of the horse. The tissue of the horse may include thyrohyoideus, geniohyoid and/or mylohyoid muscle tissue. The tissue of the horse also may include nerve tissue to the palatoglossus, palatopharyngeous, and/or thyrohyoid muscle.

Embodiments of the present invention also include an airway treatment system for treating a dorsal displacement disorder in a horse in which a pacemaker processor generates a dorsal displacement disorder treatment signal to strengthen one or more muscles involved in displacing laryngeal anatomical structure relative to the airway of a horse and susceptible to a dorsal displacement disorder. One or more stimulation electrodes then deliver the treatment signal to tissue of the horse to maintain the airway unobstructed during the exercise period.

In further such embodiments, the laryngeal anatomical structure may specifically include the larynx, epiglottis, geniohyoid muscle tissue, mylohyoid muscle tissue, and/or nerve tissue to the palatoglossus muscle, palatopharyngeous muscle, and/or thyrohyoid muscle. Displacement of a laryngeal anatomical structure relative to the airway may include reducing the distance between larynx and basihyoid bone, between the larynx and the chin, and/or between the larynx, basihyoid bone and chin simultaneously.

Embodiments of the present invention also include an airway treatment system for treating a dorsal displacement disorder in a horse in which a pacemaker processor generates a dorsal displacement disorder treatment signal to the sensory input of the temporomandibular joint innervation (trigeminal n), nasopharynx (glossopharyngeal and vagus n) and larynx (internal branch of the cranial laryngeal nerve), tongue (lingual n) to indirectly strengthen one or more muscles involved in displacing laryngeal anatomical structure relative to the airway of a horse and susceptible to a dorsal displacement disorder. One or more stimulation electrodes then deliver the treatment signal to tissue of the horse to maintain the airway unobstructed during the exercise period.

Embodiments of the present invention also include a method of using an airway treatment system for treating a dorsal displacement disorder in a horse. The method includes detecting an elevated activity level of the horse using one or more treatment sensors, generating a treatment signal based on the detected elevated activity level, using a pacemaker processor, to strengthen one or more muscles involved in displacing a laryngeal anatomical structure relative to an airway of the horse, and using one or more stimulation electrodes, configured to interface with tissue of the horse, to deliver the treatment signal to the tissue of the horse to maintain an unobstructed airway.

In some embodiments, the laryngeal anatomical structure may include the larynx of the horse and/or the epiglottis of the horse. The tissue of the horse may include one or more of geniohyoid muscle tissue, mylohyoid muscle tissue, nerve tissue to the palatoglossus muscle, nerve tissue to the palatopharyngeous muscle, thyrohyoid muscle tissue, and nerve tissue to the thyrohyoid muscle. The displacing of the laryngeal anatomical structure relative to the airway may include a reduced distance between larynx and basihyoid bone. The displacing of the laryngeal anatomical structure relative to the airway may include a reduced distance between larynx and chin. The displacing of the laryngeal anatomical structure relative to the airway may include a reduced distance between larynx and basihyoid bone and chin simultaneously. The displacing of the laryngeal anatomical structure relative to the airway may include a reduced distance between basihyoid and larynx and ventral aspect of the petrous temporal/basisphenoid bone. The method may further include recording the elevated activity level using the pacemaker processor. The method may further include monitoring the elevated activity level using the pacemaker processor, and adjusting the treatment signal based on the monitored elevated activity level. The method may further include monitoring the treatment signals using the pacemaker processor, and adjusting the treatment signal based on the monitored treatment signals. The one or more treatment sensors may include an accelerometer, an electromyogram, an electronystagmograph, an electroglottograph, an electroencephalograph, a biopotential sensor, an ultrasound sensor, a hall sensor, a microphone, a pressure sensor, a strain transducer, a mechanical deformation sensor, and/or a motion sensor. The one or more stimulation electrodes may include a cuff electrode, a multipolar cuff electrode, a tripolar cuff electrode, a flat nerve electrode, an epineural electrode, a shaft electrode, a longitudinal intrafascicular electrode, a thin wire electrode, a micro-machined electrode, and/or a sieve electrode. The one or more stimulation electrodes may be configured to cause stimulation to a specific area of the tissue of the horse by differential activation. The treatment signal may be delivered continuously over a period of hours until the system is turned off. The treatment signal may be further based on air flow characteristics of the airway tract of the horse, contractile characteristics of the airway tissue of the horse, electrical characteristics of a portion of the body of the horse, temperature of a portion of the body of the horse, pH of a portion of the body of the horse, chemical constituency of a portion of the body of the horse, and/or physiological state of the horse. The method may further include monitoring operation of the pacemaker processor using a treatment verification monitor.

DETAILED DESCRIPTION OF SPECIFIC EMBODIMENTS

Embodiments of the present invention include systems and methods for stimulating upper airway tissue of horses to relieve airway disorders such as dorsal displacement of the soft palate (DDSP), various forms of laryngeal and pharyngeal and nasopharyngeal collapse, or airway narrowing.

The exact cause of DDSP is not known, but it is believed to be caused by either direct mechanical displacement by posterior movements of the tongue, or weakness in the muscles of the soft palate or those that raise or otherwise mobilize the epiglottis, hyoid apparatus or the entire larynx. The existing standard therapy has been to raise the entire larynx closer to the hyoid bone structure. These techniques have met with only limited success, especially in the long term.

Embodiments of the present invention are based on one or more specific strategies: (1) controlling anterior movements of the tongue by stimulation of geniohyoid (genioglossus) and mylohyoid muscle or the hypoglossal nerve, (2) strengthening the muscles of the soft palate by stimulation of palatoglossus, palatopharyngeous, or neighboring pharyngeal muscles or hypoglossal, vagal or glossopharyngeal nerve branches to these muscles nerve, and/or (3) raising and/or advance the epiglottis, hyoid apparatus or the entire larynx by stimulation of geniohyoid and/or mylohyoid muscle or hypoglossal nerve and/or vagal or glossopharyngeal nerve branches to the palatoglossus, palatopharyngeous, or neighboring pharyngeal muscles; nerve branches to the thyrohyoid muscle. In this embodiment the FES either targets the effective muscles or the sensory input indirectly triggering a strengthening of the muscles controlling the aforementioned structures.

Electrical Airway Treatment System

Embodiments of the present invention include an electrical airway treatment system having an implanted portion that performs one or more functions. For example, the implanted device may generate tissue stimulation signals either by independent electronics or by dependent processing of the signal from an external component. The implant also may record sensed signals such as those related to monitoring operation of the system. In some embodiments, one or more implants may both stimulate and sense the surrounding tissue. Lead wires may be connected in a detachable or non-detachable way for transferring the stimulation signals to the electrodes or recording signals from the electrodes and/or the sensors.

Figure 1:
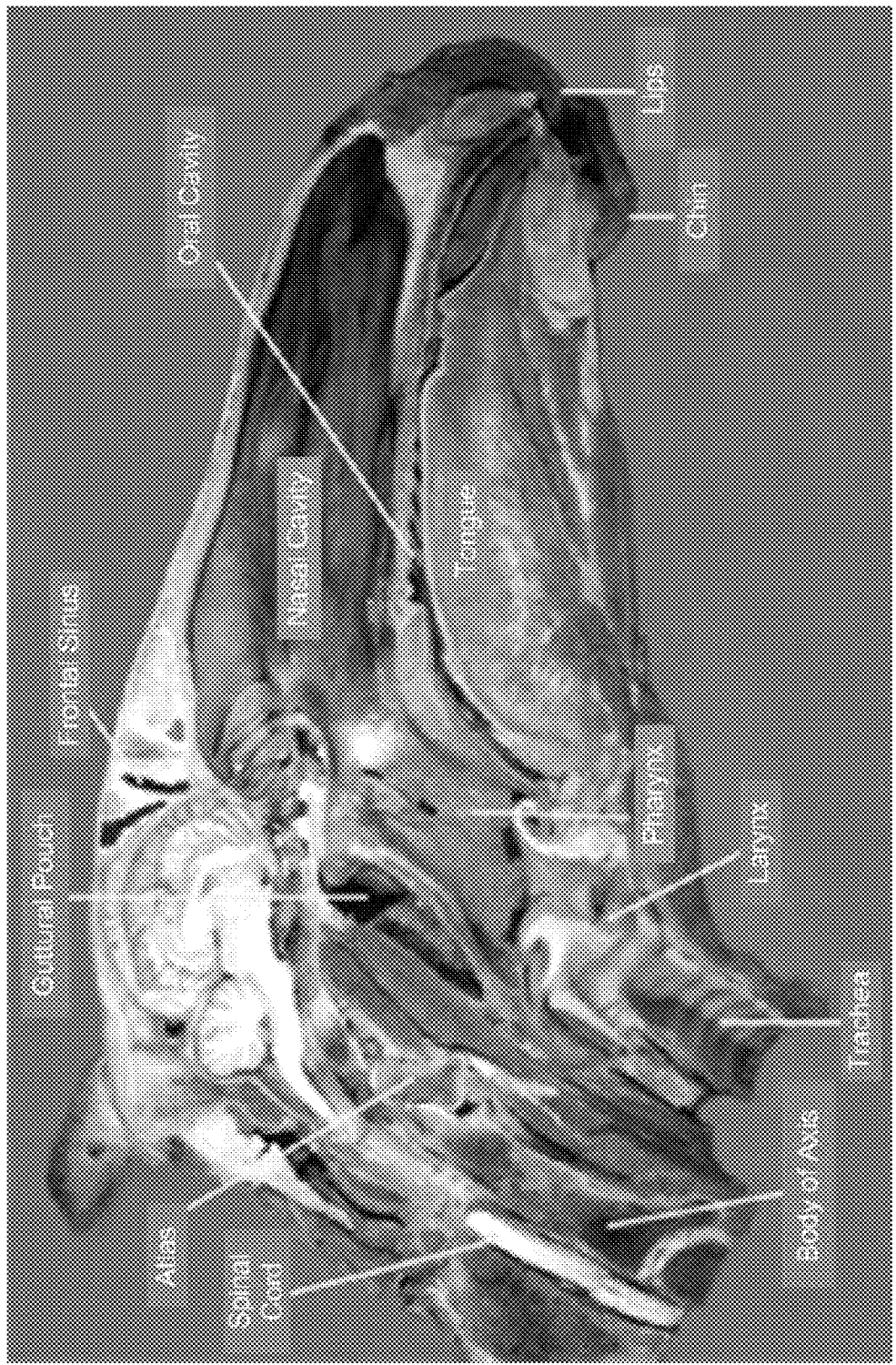
FIG. 1 shows various anatomical structures in the head of a horse.
Figure 2:
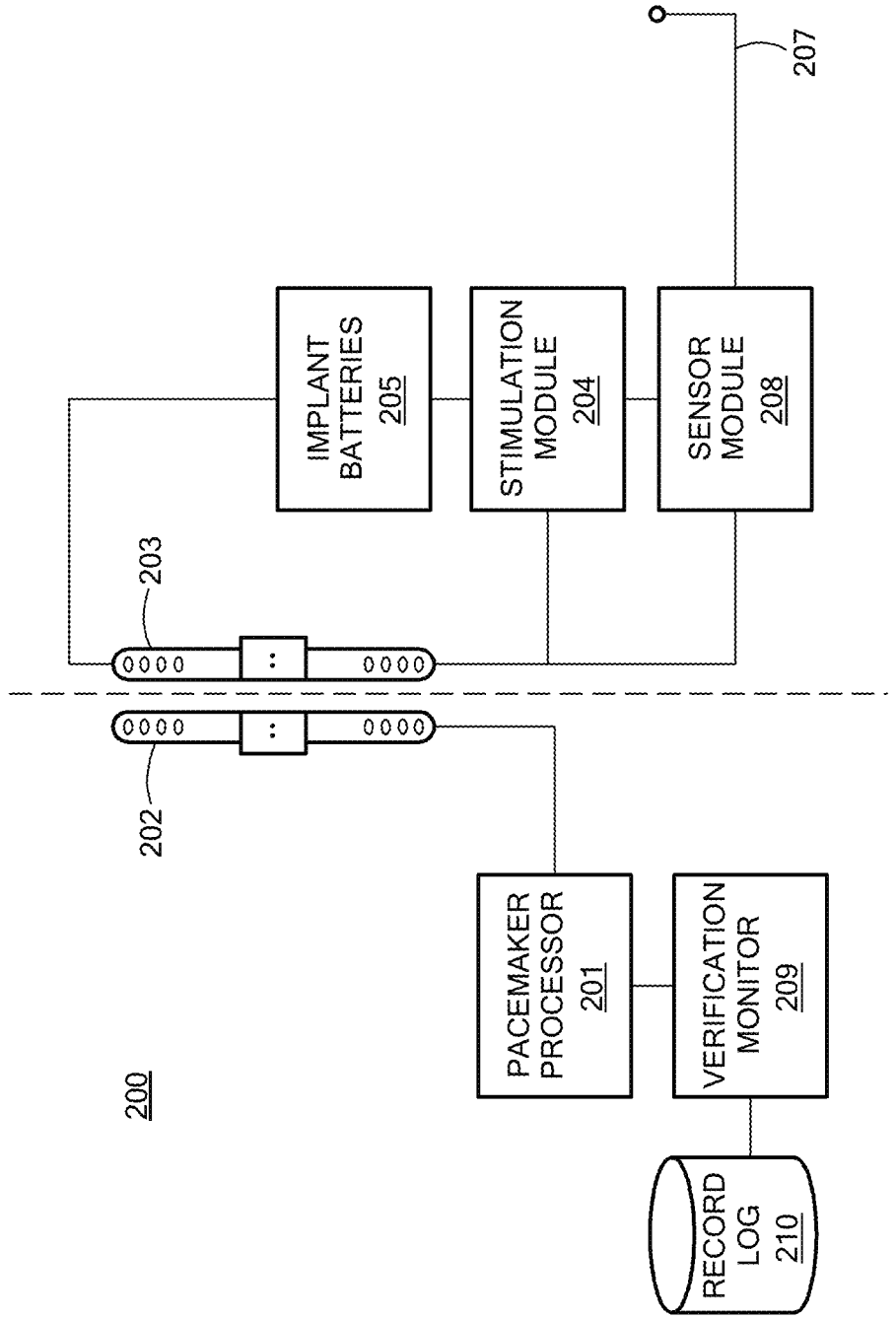
FIG. 2 shows of various functional blocks involved in representative embodiments of an airway treatment system for horse airway disorders.

FIG. 2 shows an example of various functional blocks involved in representative embodiments of an airway treatment system 200 for horse airway disorders. A pacemaker processor 201 generates an electrical treatment signal to be applied to upper airway tissue of the horse for treating the upper airway disorder. The pacemaker processor 201 may perform other useful functions, including without limitation, monitoring and analysis of stimulation signals, sensor signals, and/or other treatment signals. The pacemaker processor 201 may also provide a programmable interface for adjusting other elements within the system and control the functioning of such other elements.

The pacemaker processor 201 in FIG. 2 is an external element of the system, for example, in a housing on the skin of the horse or integrated into the horse's harnessing. In other specific embodiments, the pacemaker processor 201 may be implanted within the horse. In an external embodiment such as the one shown in FIG. 2, the pacemaker processor 201 provides the treatment signal (as well as any other signals useful for the implanted portion of the airway treatment system 200, e.g., a power signal) to an external coil 202 which inductively couples the signal(s) to a corresponding internal coil 203. Such coil arrangements are similar to those which are well known in the field of human cochlear implants.

The treatment signal received by the implanted coil 203 is input to a stimulation module 204 which develops an electrical treatment signal for application by one or more stimulation electrodes 206 which interface with the targeted upper airway tissue associated with the upper airway disorder being treated. The stimulation module 204 may be turned on to work continuously until turned off. Or the stimulation module 204 may be triggered by a signal obtained from the animal including but not limited to the following.

The embodiment in FIG. 2 also has a sensor electrode 207 which is senses one or more therapy parameters related to the operation of the airway treatment system 200. For example, airflow characteristics and other physiological data. The sensor electrode 207 signal is processed by a sensor module 208 which may provide feedback to the stimulation module 204 and/or back to the pacemaker processor 201 (e.g. via load modulation from the internal coil 203 back to the external coil 202). The feedback signal from the sensor electrode 207 may be used by external components of the system such as generally by the pacemaker processor 201, or more specifically by a treatment verification monitor 209 which verifies proper operation of the airway treatment system 200, for example, to ensure compliance with wagering related safeguards which may be required by one or more regulatory bodies, or more generally, monitor operation of the airway treatment system 200 based on information received from various system components. The airway treatment system 200 may also include a record log 210 which records various information related to operation of the airway treatment system 200 such as periodic values of the one or more therapy parameters from the sensor electrode 207.

Specific embodiments of the airway treatment system 200 may be totally external on the horse, totally implanted, or have both the external and internal components. Embodiments of a airway treatment system 200 with both external and internal components can transfer information and/or energy across the skin of the horse. The external components may be fixed permanently to the skin of the horse, or placed temporarily when the stimulation module 204 is functional, or placed intermittently, for example, to charge the implant battery 205, to program the stimulation module 204, or to turn the stimulation module 204 on and off.

Example embodiments include but are not limited to airway treatment systems 200 that transfer energy or information across the skin transcutaneously or percutaneously. Percutaneous systems have direct wiring or equivalent hardware that transfers information and energy across skin or mucosa. Generally, chronic foreign objects placed across skin or mucosa risk becoming infected. However, newer technologies known in the art allow the in growth of skin or mucosa onto the surface of the wire to protect the percutaneous entry of the wires. For cosmetic purposes, the percutaneous device may appear to be a decorative piercing, such as earrings are used by humans.

Alternatively or in addition, the implanted and the external components of the airway treatment system 200 may be transcutaneously linked, for example, as shown in FIG. 2 by an external coil 202 and a corresponding internal coil 203. Besides an arrangement of electromagnetic induction coils such as that shown in FIG. 2, transcutaneous systems known in the art include acoustic energy, optical energy (e.g., U.S. Pat. No. 5,387,259), and/or capacitor coupling approaches. There may be an energy and/or data transfer system which interconnects a transcutaneous link with a first implanted component, and a transducer system of the first implanted component and the second implanted component (for example the stimulation module 204). An example of such a airway treatment system 200 includes but is not limited to a first inductive link from the external components to the first implanted coil 203 and an implanted connection to an implanted second inductive link to the implanted stimulation module 204. This arrangement may be useful to change parts of the airway treatment system 200, for example, in the case of malfunctions or upgrades, or to have a 2 phase implantation procedure of different components of the airway treatment system 200.

Internal and components of the airway treatment system 200 also may communicate using ultrasonic vibrations or magnetic fields. For example, a magnetic coupler may add electrical energy to an inductive demodulation module to directly power the implanted components, or a capacitor or rechargeable battery may receive such energy and store it for later use.

External components can serve various functions such as changing or adapting parameters of the implanted portions of the airway treatment system 200. The external components may be placed under or within blinders or other racing gear of the horse. Besides the specific arrangement shown in FIG. 2, other examples of the external components may include induction coils, electronic circuitry, radio telemetry equipment, a detecting system, a processor, and a power source (e.g., a battery). In specific embodiments, the external components may transmit electrical power signals only (e.g., to recharge the implant battery 205), data signals only (e.g., stimulation signals for the stimulation module 204), control signals only (e.g., controlling or changing parameters of implanted components such as the stimulation module 204, stimulation electrodes 206, and/or sensor electrode 207), or any combination thereof.

The external and internal components require appropriate mechanical fixation to remain attached during vigorous exercise. In addition, movement of the components stresses any wires leading to or away from the component potentially causing the wire to break. Examples of methods of the external fixation include glues, tapes, sutures, magnets, piercings, bands around the animal, or utilizing existing equine equipment such as the bridle, blinders, mane tamer, and saddle. As a non-limiting example the external coil 202 may be placed on the bridle of a horse in the area overlying the implanted the implant coil 203.

The airway treatment system 200 may use an electromyogram (EMG) of another inspiratory muscle, and it may include: a) a sensor electrode 207 adapted for electrical coupling to a normally functioning muscle which contracts during inspiration, and for providing electrical signals indicative of muscle activity thereof; b) a stimulation electrode 206 for electrical coupling to a dysfunctional muscle; c) a pacemaker processor 201 to receive the sensing signals from the sensor electrode 207 and provide the stimulating signals to the stimulation electrode 206. The dysfunctional muscle, in pacemaker operation, is stimulated in substantial synchronism with the activity of the normally functioning muscle. A normally functioning muscle which contracts during inspiration could be the contralateral healthy muscle, or the diaphragm muscle or other muscles showing a high correlation of their EMG to inspiratory signals.

Or the airway treatment system 200 may be based on electronystagmography (ENG) and include: a) a sensor electrode 207 adapted for electrical coupling to a normally functioning nerve which contracts during inspiration and providing electrical signals indicative of nerve activity thereof; b) a stimulation electrode 206 for electrical coupling to a dysfunctional muscle; c) a pacemaker processor 201 coupled to receive the sensing signals from the sensor electrode 207 and for providing the stimulating signals to the stimulation electrode 206 in substantial synchronism with the electrical signals provided by the sensor electrode 207. The dysfunctional muscle, in pacemaker operation, is stimulated in substantial synchronism with the activity of the normally functioning nerve. A normally functioning nerve which contracts during inspiration could be the phrenic nerve or other nerves showing a high correlation of their ENG to inspiratory signals.

An airway treatment system 200 may be based on electroglottography (EGG) and may include: a) sensing electrodes 207 adapted for electrical coupling to measure vocal fold contact area (called electroglottography—EGG). EGG involves a high frequency, low current signal passed between the vocal folds with the aid of electrodes. Sensing electrodes 207 are placed on either side of the thyroid lamina or closer to the vocal folds. EGG is based on the principle that tissue conducts current. Therefore, when the vocal folds touch, greater current flows. The output of the electroglottographic recordings can be used to determine when the vocal folds are closed or opened and how fast they are closing or opened) for providing electrical signals indicative of vocal fold opening; b) a stimulation electrode 206 for electrical coupling to a dysfunctional muscle; c) a pacemaker processor 201 to receive the sensing signals provided by the sensing electrodes 207, and for providing the stimulating signals to the stimulation electrode 206. The dysfunctional muscle, in pacemaker operation, is stimulated in substantial synchronism with the activity of the vocal fold opening signal.

Or an airway treatment system 200 may be based on using an electroencephalogram (EEG), and it may include: a) sensing electrodes 207 adapted for measurement of electrical activity in the brain, recording from electrodes placed on, in or under the scalp, or subdurally, or in the cerebral cortex with the sensing electrodes 207 located in areas where the EEG represents an electrical signal (postsynaptic potentials) from a large number of neurons showing a high correlation to inspiratory signals during inspiration and for providing electrical signals indicative of activity thereof; b) a stimulation electrode 206 for electrical coupling to a dysfunctional muscle; c) a pacemaker processor 201 to receive the sensing signals provided by the sensing electrodes 207, and for providing the stimulating signals to the stimulation electrode 206. The dysfunctional muscle, in pacemaker operation, is stimulated in substantial synchronism with the activity of the normally functioning brain region activity.

Or an airway treatment system 200 may be based on biopotentials, and it may include: a) sensing electrodes 207 to measure biopotentials for electrical signals with a high correlation to vocal fold opening or the amount of airflow during inspiration; b) a stimulation electrode 206 for electrical coupling to a dysfunctional muscle; c) a pacemaker processor 201 to receive the sensing signals from the sensing electrodes 207, and for providing the stimulating signals to the stimulation electrode 206.

Electrode Implementation

Implant system electrodes such as the sensing electrodes 207 and/or the stimulation electrode 206 can be placed on one or more of the nerve branches of the hypoglossal nerve to the genioglossus, geniohyoid, hyoepiglotticus; vagal or glossopharyngeal nerve branches to the palatoglossus, palatopharyngeous, or neighboring pharyngeal muscles; nerve branches to the thyrohyoid muscle. Alternatively, the sensing electrodes 207 and/or the stimulation electrode 206 can placed directly in or around the above described muscles, or on, under, or in the vicinity of upper airway mucosa. Electrical stimulation signals are then applied to mucosa or the sensory nerves supplying mucosa to evoke a swallow or reflex motor changes.

For example, in the treatment of nasopharyngeal collapse, the sensing electrodes 207 and/or the stimulation electrode 206 can be placed on or around the nerve branch to the stylopharyngeus muscle that forms the roof of the nasopharynx and the palatopharyngeous muscle that forms the walls of the nasopharynx. Or for treatment of epiglottic retroversion, the sensing electrodes 207 and/or the stimulation electrode 206 can be placed on or around the nerve branch to the hyoepiglotticus muscle and stimulation applied to retract the epiglottis anteriorly. Or the sensing electrodes 207 and/or the stimulation electrode 206 may be placed on or around the hyoepiglotticus muscle. (NB: All muscles are bilateral here and may or may not need bilateral stimulation.)

The sensing electrodes 207 and/or the stimulation electrode 206 may be placed on the skin or mucosa of the animal, or within the body closer to the target tissue. For example, the sensing electrodes 207 and/or the stimulation electrode 206 may be directly adjacent to the target nerve where they will be very efficient and avoid spreading current to surrounding tissue. Multiple stimulation electrodes 206 can be placed around the tissue such that differential activation of the stimulation electrodes 206 can cause the current to flow through specific areas of the target, thereby activating a portion of the target. This may be referred to as a steerable electrical field. An example of the use of such a stimulation electrode 206 is to activate a portion of a nerve containing the neurons to a specific muscle while leaving the remaining neurons unstimulated.

Figure 3A:
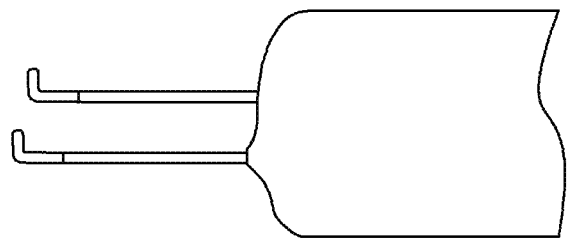
FIG. 3A-C shows some non-limiting examples of specific electrode arrangements that may be useful.

FIG. 3A-D shows some non-limiting examples of specific arrangements of the sensing electrodes 207 and/or the stimulation electrode 206 that may be useful. For example, a pair of electrodes may stimulate small nerve branches to confirm their function, as shown in FIG. 3A, where the electrodes are 2 mm apart and bent in order to hook and isolate small nerves for stimulation.

Figure 3B:
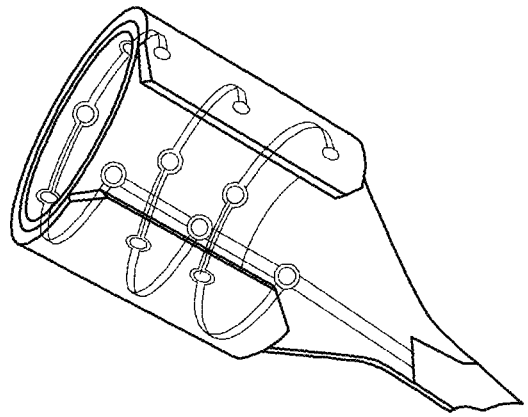

Another type of less invasive electrode is the cuff electrode, an example of which is shown in FIG. 3B. This kind of electrode can be placed around the peripheral nerve or in the spinal cord like an open tube. The electrodes are thus positioned inside the cuff in close contact with the nerve. But in such an embodiment, a contraction may place the epineurium covering the nerve between the electrode and the fibers. The epineurium works as a kind of electrical insulator, so this would reduce the recording signals and increases stimulation thresholds.

Multipolar cuff electrodes can be used for selective stimulation such that different fascicles of a nerve can be stimulated. For example, a cuff electrode with one electrode ring each at the distal, proximal, and central positions of the tube may be useful for recording neural signals and/or for nerve stimulation. For recording, multiple cuff electrodes allow suppression of the external noise sources such as line interface or bioelectrical muscle signals by using the electrode in combination with a specific amplifier configuration. For stimulation, this configuration limits the spread of electric current outside the cuff.

An alternative embodiment uses a flat nerve electrode similar to a cuff, but with a flat cross section. For example, see D. J. Tyler, D. M. Durand, *Functionally Selective Peripheral Nerve Electrode: Stimulation With A Flat Interface Nerve Electrode*, IEEE Transactions On Neural Systems And Rehabilitation, 2002 10 (4), pp 294-303, incorporated herein by reference. By flattening the nerve, the nerve fascicles are more separated and more selective stimulation and recording is possible. This also improves selectivity. Another embodiment uses an epineural electrode which is sutured to the epineurium of the nerve, an arrangement which is that is very efficient and selective.

Figure 3C:
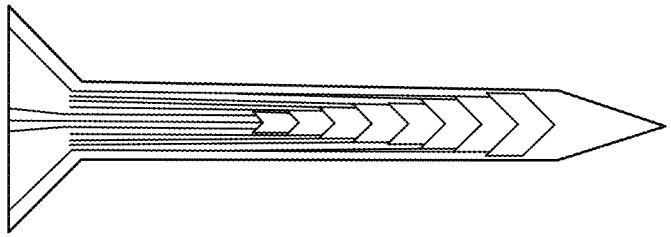

FIG. 3C shows an example of a shaft electrode which may be more invasive than cuff electrodes (See, e.g., T. Stieglitz, M. Gross, *Flexible BIOMEMS With Electrode Arrangements On Front And Back Side As Key Component In Neural Prostheses And Biohybrid Systems*, Transducers '01/Eurothe sensors XV, 358-361, 2001, incorporated herein by reference). The electrodes have a needle shape with multiple sides. The electrodes are inserted into the neural tissue for closer contact between the electrode side and the nerve fibers. One difficulty though is the implantation method because of the mechanical stiffness of the peripheral nervous system. Further approaches are under development to improve the stability and the penetration properties of this kind of electrodes. Additionally new implantation tools would be useful.

Figure 9:
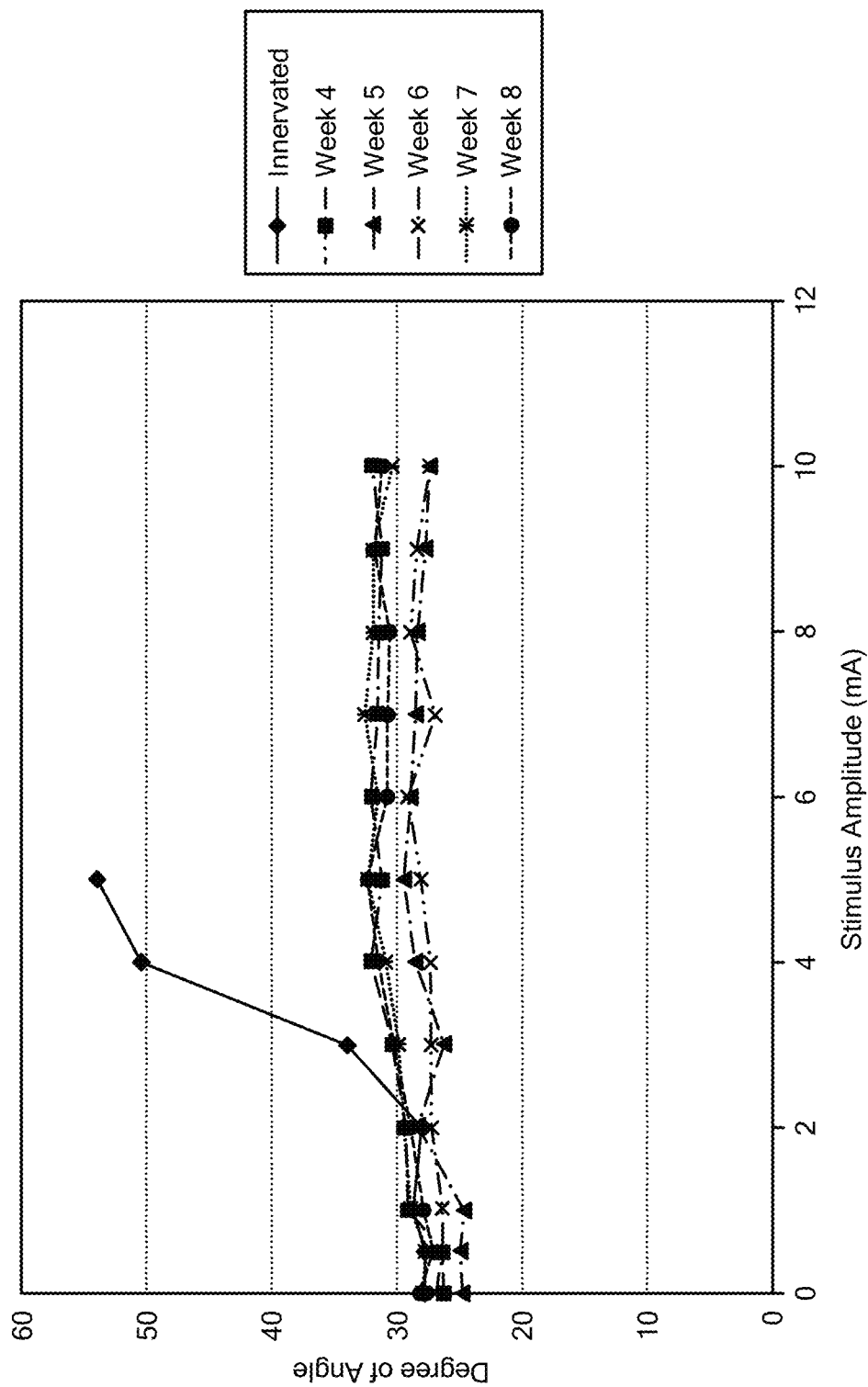
FIG. 9 shows D-VDR (50 Hz, 6 ms) for one set of experiments.

A longitudinal intrafascicular electrode combines a loop of a thin wire electrode with a filament loop including a thin needle. This needle can be used for guidance to implant the thin film electrode longitudinally into the nerve. Only the thin wire electrode will be left into the nerve. Depending on the implantation of the electrode a high selectivity can be achieved. See, e.g., K. Yoshida, D. Pellinen, P. Rousche, D. Kipke, *Development Of The Thin-Film Longitudinal Intra-Fascicular Electrode*, Proceedings Of The 5th Annual Conference Of The International Functional Electrical Stimulation Society, pp 279-281, 2000, incorporated herein by reference. Limitation to a low number of electrode sites for longitudinal intrafascicular electrodes can be resolved by the use of polyimide substrates as shown in FIG. 9. The number of electrodes can be increased by the use of micro-structuring technologies. Moreover, a reference electrode and ground electrodes may be included on the substrate.

As an alternative to thin-film electrodes, micro-machined electrodes based on silicon may be used as needle arrays. At least two approaches are under development. One approach uses a combination of sawing and etching to structure a wafer from the normal direction; see, e.g., R. A. Normann, E. M. Maynard, P. J. Rousche, D. J. Warren, *A Neural Interface For A Cortical Vision Prosthesis*, Vision Research, 39, 2577-2587, 1999, incorporated herein by reference. The second approach structures a wafer in planar direction; see, e.g., K. D. Wise, D. J. Anderson, J. F. Hetke, D. R. Kipke, K. Najafi, *Wireless Implantable Microsystems: High-Density Electronic Interfaces To The Nervous System*, IEEE Proceedings (Invited Paper) Vol. 93 No. 1, 2004, incorporated herein by reference. This allows combination of the electrodes and the electronics. Many electrodes can be placed on each needle. One drawback of this kind of electrode is that the basic structure is only an arrangement of needles. A batch is required to create an array. For the silicon electrode arrays, special implantation tools may be needed to implant the arrays at high speed.

One invasive kind of electrode is the sieve electrode; see, e.g., A. Ramachandran, O. Brueck, K. P. Koch, T. Stieglitz, *System Test Of A Smart Bi-Directional Interface For Regenerating Peripheral Nerves*, Proceedings 9th Annual Conference Of IFES Society, Bournemouth, pp 425-427, 2004, incorporated herein by reference. This electrode will be placed between two cut ends of a nerve trunk. For guidance and fixation to the nerve, silicone tubes may be placed on both sides of the sieve; see, e.g., P. Dario et al., *Robotics As A Future And Emerging Technology: Biomimetics, Cybernetics And Neuro-Robotics In European Projects*, IEEE Robotics And Automation Magazine, Vol. 12, No. 2, pp 29-45, 2005; and X. Navarro et al., *Stimulation And Recording From Regenerated Peripheral Nerves Through Polyimide Sieve Electrodes*, J Peripher Nerv Syst. 3 (2) pp 91-101, 1998, incorporated herein by reference. The nerve fibers then regenerate through the holes of the sieve electrode. Some of the holes may be constructed with ring electrodes to contact the nerve fibers. With regards to implantation, the applications for such electrodes include amputees and basic research; see, e.g., P. Dario et al., *Neural Interfaces For Regenerated Nerve Stimulation And Recording*, IEEE Trans. Rehab. Eng, Vol. 6, No. 4, pp. 353-363, 1998, incorporated herein by reference.

Figure 4:
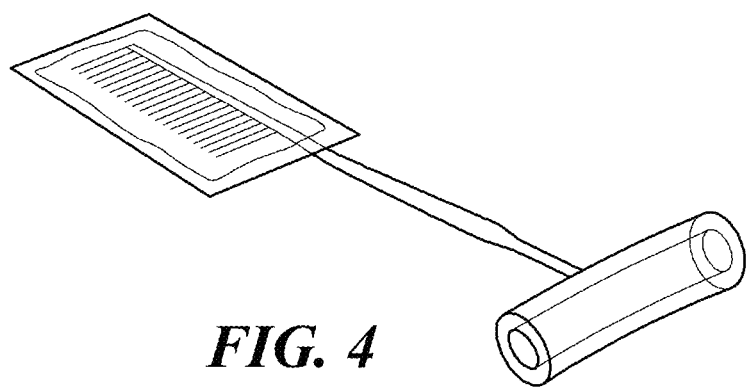
FIG. 4 an example of a sieve electrode used to contact the fibers of regenerating nerves.

FIG. 4 shows an example of a sieve electrode used to contact the fibers of regenerating nerves. By placing the micro sieve in the regeneration pathway, the fibers regenerate through the different holes of the sieve electrode. Ring-shaped electrodes around the sieve holes can have a close contact to this regenerated fibers. In that case, a selective coupling of the sensory and motor is possible; see, e.g., P. Negredo, J. Castro, N. Lago, X. Navarro, *Differential Growth Of Axons From The Sensory And Motor Neurons Through A Regenerative Electrode: A Stereological, Retrograde Tracer, And Functional Study In The Rat*, Neuroscience pp. 605-615 (2004), incorporated herein by reference. As a result, selective stimulation and recording of neural bioelectrical potentials could be achieved. An example of an electrode that can steer current is the perineural ring electrode.

Figure 5:
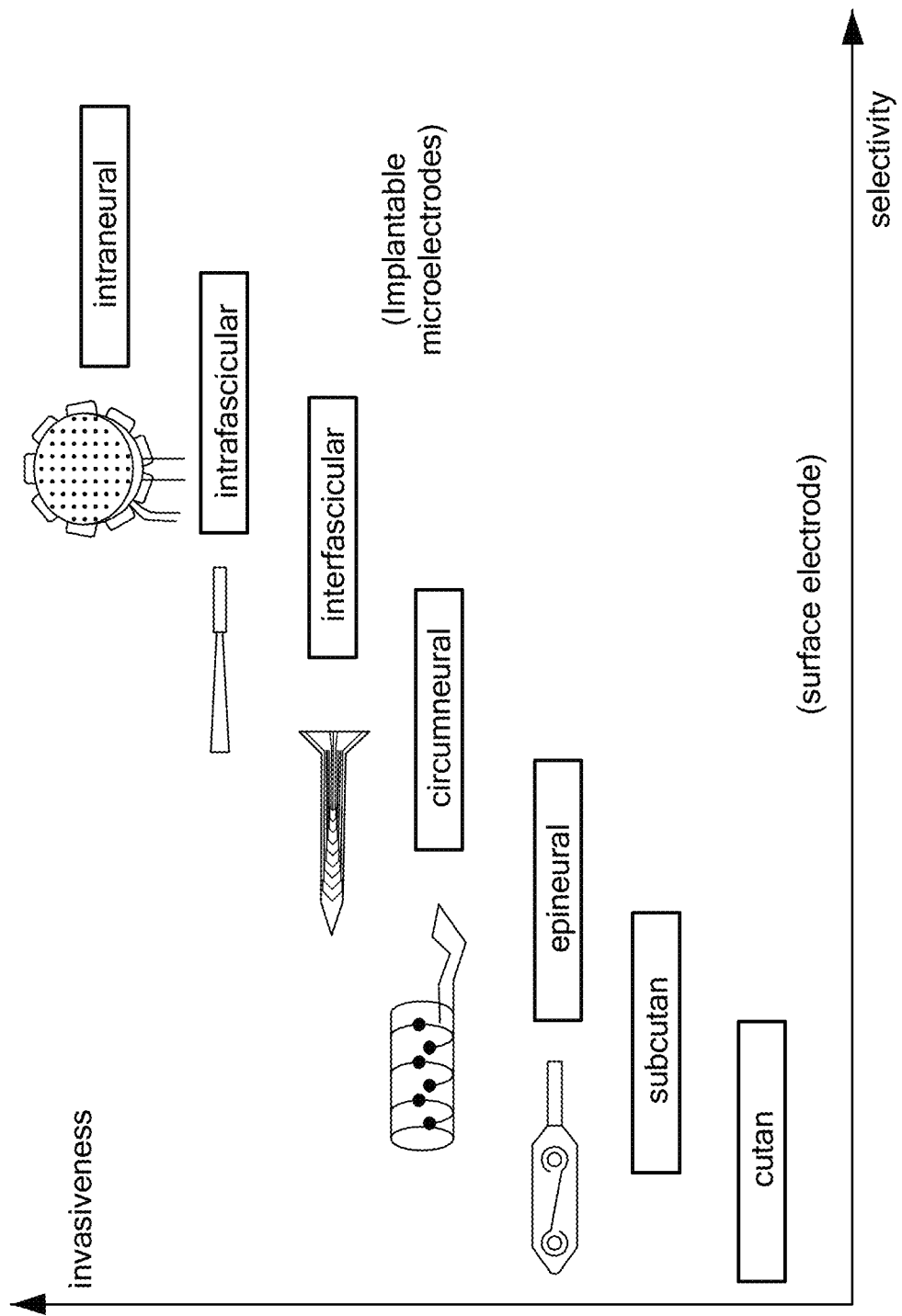
FIG. 5 summarizes for various possible specific electrode configurations the tradeoffs and relative interaction between electrode selectivity and invasiveness to the affected tissue.

FIG. 5 summarizes for various possible specific electrode configurations the tradeoffs and relative interaction between electrode selectivity and invasiveness to the affected tissue.

Possible Sensors Alternative to Electrodes:

Ultrasound sensing can also be used in an embodiment of a treatment system 200 including: a) sensing electrodes 207 for ultrasound coupling to the vocal fold area or pharynx or the lungs or other regions in the body having a movement or volume change with high correlation to inspiration; b) a stimulation electrode 206 for electrical coupling to a dysfunctional muscle; c) a pacemaker processor 201 to receive the sensing signals provided by the sensing electrodes 207, and for providing the stimulating signals to the stimulation electrode 206.

An embodiment of a treatment system 200 may be based on sensors that use the Hall effect. The Hall effect refers to the potential difference (Hall voltage) on opposite sides of a thin sheet of conducting or semiconducting material in the form of a 'Hall bar' (or a van der Pauw element) through which an electric current flows. This is created by a magnetic field applied perpendicular to the Hall element. The potential difference is correlated to the strength of the magnetic field. The strength of the magnetic field can be influenced by the transmission of the magnetic field, by tissue changes or movement of tissue composed of parts with different conductivity near the semiconducting Hall the sensor element, or by distance or orientation changes of the Hall the sensor and the source of the magnetic field relative to each other.

Another embodiment could have a treatment system 200 including: a) a sensing microphone for generating an electrical signal representative of activity in an internal sensing location coupling to the vocal fold area, pharynx, lungs, or other regions in the body having a movement or volume change with high correlation to inspiration; b) a stimulation electrode 206 for electrical coupling to a dysfunctional muscle; and c) a pacemaker processor 201 to receive the sensing signals provided by the sensing microphone, and for providing the stimulating signals to the stimulation electrode 206. See, e.g., U.S. Pat. No. 6,174,278.

An embodiment may also be a treatment system 200 based on pressure sensing including: a) a pressure sensor for generating an electrical signal representative of activity in an internal sensing location coupling to the vocal fold area, pharynx, lungs, or other regions in the body having a movement or volume change with high correlation to inspiration; b) a stimulation electrode 206 for electrical coupling to a dysfunctional muscle; c) a pacemaker processor 201 to receive the sensing signals provided by the pressure sensor, and for providing the stimulating signals to the stimulation electrode 206.

A strain transducer can be used in a treatment system 200 including: a) a strain transducer for generating an electrical signal representative of elongations or compression in an internal sensing location coupling to the vocal fold area, pharynx, larynx, thorax, lungs, or other regions in the body having a movement or volume change with high correlation to inspiration; b) a stimulation electrode 206 for electrical coupling to a dysfunctional muscle; c) a pacemaker processor 201 to receive the sensing signals provided by the strain transducer, and for providing the stimulating signals to the stimulation electrode 206.

Torsion or bending can also be used in a treatment system 200 including: a) a mechanical deformation sensor for generating an electrical signal representative mechanical stress in an internal sensing location coupled to the vocal fold area, pharynx, larynx, thorax, lungs, or other regions in the body having a movement or volume change with high correlation to inspiration; b) a stimulation electrode 206 for electrical coupling to a dysfunctional muscle; c) a pacemaker processor 201 to receive the sensing signals provided by the mechanical deformation sensor, and for providing the stimulating signals to the stimulation electrode 206.

For example, a torsion or bending based treatment system 200 could use a piezo-active material. Piezoelectricity is the ability of certain crystals to generate a voltage in response to applied mechanical stress. The piezoelectric effect is reversible in that piezoelectric crystals, when subjected to an externally applied voltage, can change shape by a small amount. The deformation, about 0.1% of the original dimension, typically is of the order of nanometers, but nevertheless finds useful applications such as in the production and detection of sound, generation of high voltages, electronic frequency generation, and ultra-fine focusing of optical assemblies. In a piezoelectric sensor, a physical dimension is transformed by an applied mechanical force which acts on two opposing faces of the sensing element. Depending on the design of the sensor, different "modes" to load the piezoelectric element can be used: longitudinal, transversal, and shear.

The piezoresistive effect differs from the piezoelectric effect. The piezoresistive effect describes the changing electrical resistance of a material due to applied mechanical stress. In contrast to the piezoelectric effect, the piezoresistive effect only causes a change in resistance, but does not produce electrical charges. That is done by an additional electrical circuit.

In a typical system, electrodes/sensors may be inserted into muscles that attach to the same solid anatomical structure such as cartilage or bone available to the upper respiratory system. This allows for two axis control of the attached solid anatomical structure when the muscles are stimulated.

In addition, the muscle groups of the equine upper respiratory system include muscles that create forces where they are attached to the bone and that modify the resultant movement with respect to each other. Pairs of muscles may coordinate to create a complicated movement of the commonly attached structure such as the hyoid bone. So even though there may be many individual muscles attached to the same structure, electrical stimulation of just two muscles may produce normal movement or nearly normal movement. So rather than stimulating just one muscle, controlling two muscles together may be more effective; for example, stimulating the geniohyoid muscle together with a second muscle. Similarly, it may also be advantageous to stimulate three or more muscles together as a group. For example, two muscles may be controlled together as a coordinated pair and then a third muscle included in the stimulation arrangement to apply a force that modifies or augments the effects of the coordinated pair of muscles. Or a pair of opposing muscles may be alternately stimulated and modified or controlled by a third muscle.

Specifically, it may be useful to electrically stimulate a near-center attached muscle and an off-center attached muscle. For example, stimulation of the near-center attached geniohyoid muscle together with another off-center attached muscle may usefully produce a reduced distance of the hyoid complex and the larynx relative to the chin to protect the airway. There may also be movement of other biaxial cartilages and bones of the upper airway by electrical stimulation of two or more coordinating muscles.

Two or more muscles may be stimulated using different voltages, currents, pulse patterns and periodicities. A given muscle may respond differently between one animal and another. Still these different individual responses may be accounted and compensated for. for example, using feedback signals measuring the stimulation effects; for example, a two-axis digital image of a portion of the upper airway may be used to determine the effect of electrical stimulation of one or more muscles. Or a useful feedback sensing arrangement may be based on a direct electrophysiological measurement from another feedback electrode at a separate location in the same muscle.

Among the potential target tissue locations for electrical stimulation and/or sensing are striated muscles attached to ligaments and tendons which move bones, or to cartilage. Examples of such potential locations include without limitation the mylohyoid, thyrohyoid, geniohyoid, hyoglossus, palatopharyngeous, cricopharyngeus, inferior constrictor, superior constrictor, anterior and posterior bellies of the digastric, genioglossus, temporalis, levator veli palatini, tensor veli palatini, palatoglossus, inferior longitudinal and superior longitudinal muscles of the tongue, styloglossus, thyroarytenoid, lateral cricoarytenoid, and interarytenoid muscles.

Useful combinations of multiple muscles include without limitation the bilateral mylohyoid muscle(s), the bilateral thyrohyoid muscle(s), the bilateral geniohyoid muscle, the unilateral mylohyoid muscle(s), the unilateral geniohyoid muscle(s), the unilateral thyrohyoid muscle(s), the geniohyoid and thyrohyoid muscle combination, the mylohyoid and thyrohyoid muscle combination, the geniohyoid and the mylohyoid muscle combination. Mylohyoid stimulation refers to stimulation that creates thyroid prominence movement closer to the chin and segmental tissue retraction. Geniohyoid stimulation refers to stimulation that creates inferior-anterior bulking of segmental tissue without producing tongue movement or jaw lowering. Thyrohyoid stimulation refers to stimulation that creates reduced distance between the hyoid complex larynx and a slight diagonal twisting of the thyroid prominence contralateral to the side of stimulation.

Thus DDSP treatment may be based on displacement of a laryngeal anatomical structure relative to the airway to raise the laryngeal anatomical structure and maintain the airway unobstructed during the exercise period. Specific examples of the raised laryngeal anatomical structure may without limitation include the larynx and/or epiglottis of the horse. The stimulated tissue may without limitation include geniohyoid and/or mylohyoid muscle tissue. The tissue of the horse also may include nerve tissue to the palatoglossus, palatopharyngeous, and/or thyrohyoid muscle.

Embodiments of the present invention also include an airway treatment system for treating a dorsal displacement disorder based on generating a treatment signal to strengthen one or more muscles involved in displacing laryngeal anatomical structure relative to the airway of a horse and susceptible to a dorsal displacement disorder. Specific examples of the laryngeal anatomical structure which is treated may without limitation include the larynx, epiglottis, geniohyoid muscle tissue, mylohyoid muscle tissue, and/or nerve tissue to the palatoglossus muscle, palatopharyngeous muscle, and/or thyrohyoid muscle. The displacement of the laryngeal anatomical structure relative to the airway may include reducing the distance between larynx and basihyoid bone, between the larynx and the chin, and/or between the larynx, basihyoid bone and chin simultaneously.

Figure 7:
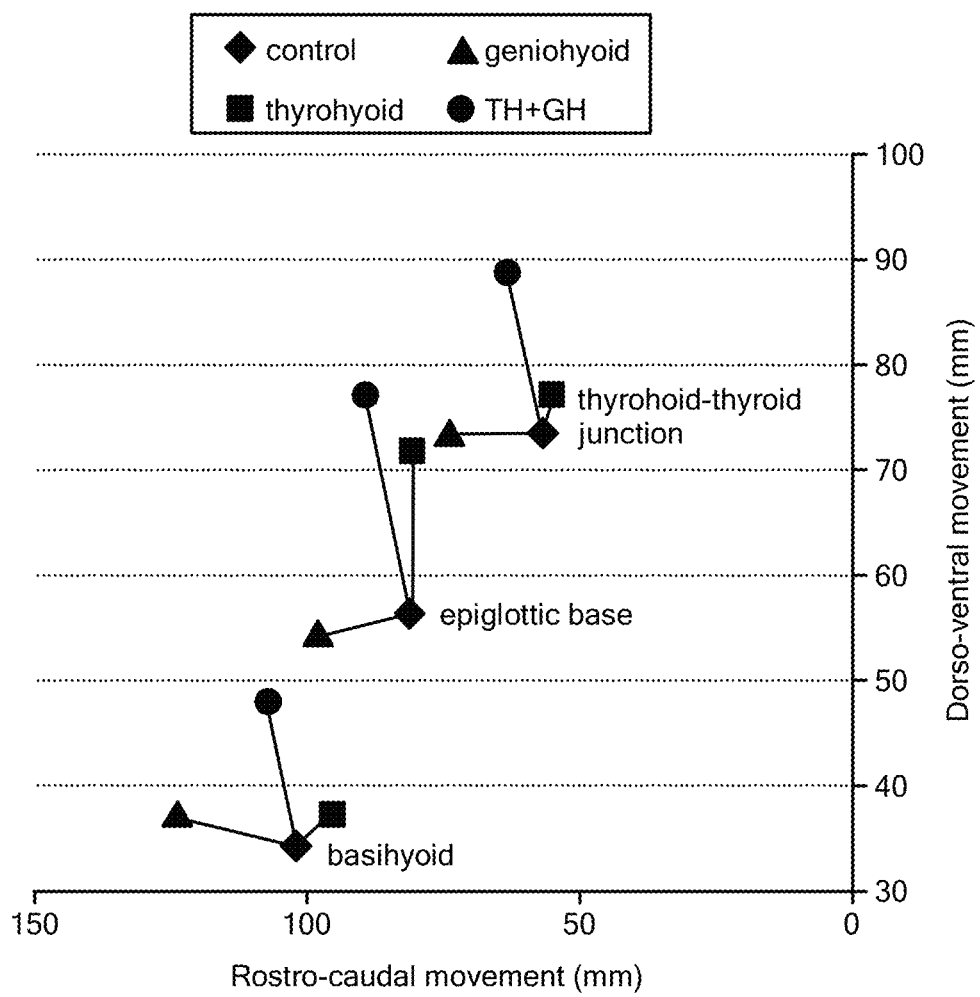
FIG. 7 shows a radiographic assessment of the effects of muscle stimulation on three laryngeal points.
Figure 8:
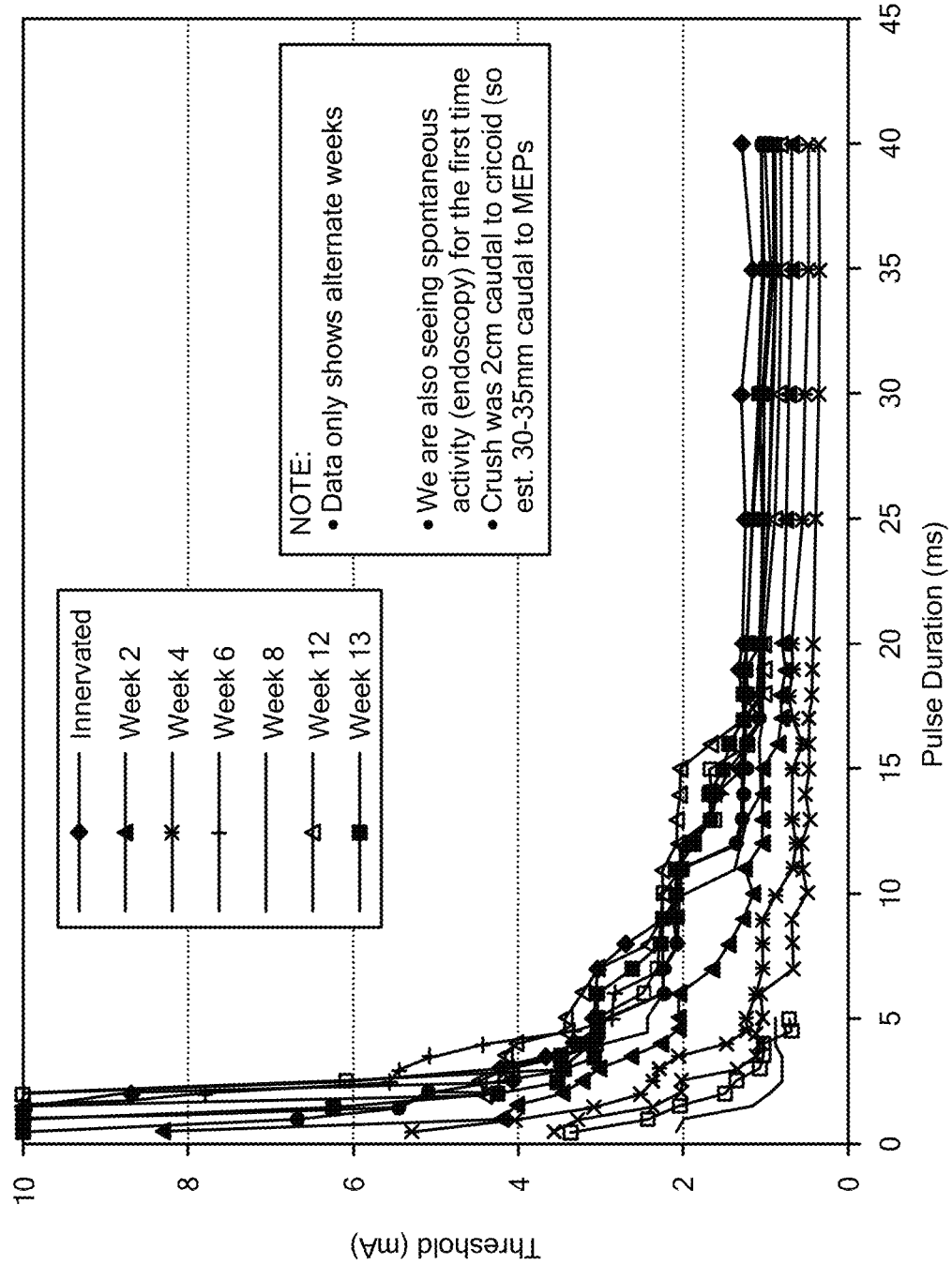
FIG. 8 shows a D-strength duration curve over time for one set of experiments.

FIG. 7 shows a graph of data measurements for one set of experiments illustrating the effect of muscle stimulation on three laryngeal points. The measurements were taken radiographically showing in millimeters rostro-caudal movement versus dorso-ventral movement, comparing against control data for stimulation of the thyrohyoid muscle, the geniohyoid muscle, and stimulation together of both the thyrohyoid and geniohyoid muscles. FIG. 8 shows a D-strength duration curve over time for a similar set of experiments, and FIG. 9 shows D-VDR (50 Hz, 6 ms) for a set of experiments.

Another small set of experiments tested treatments of horses with naturally occurring DDSP exploring muscle pacing of the thyrohyoideous muscle alone, the geniohyoideous muscle pacing alone, simultaneous pacing of the thyrohyoideous muscle and geniohyoideous muscle, hypoglossal nerve pacing (the hypoglossal nerve innervates all protrusion and retraction muscles of the tongue including the thyrohyoideous and geniohyoideous), and simultaneous pacing of the thyrohyoideous muscle and hypoglossal nerve cuff. These experiments demonstrated that hypoglossal nerve stimulation co-contracts all the tongue muscles including protrusion and retraction muscles and caused even more palatal displacements. Independent stimulation of the thyrohyoideous muscle, geniohyoideous muscle, or genioglossus muscle reduced the number of palatal displacements.

Parametric Adjustment Techniques

Figure 6:
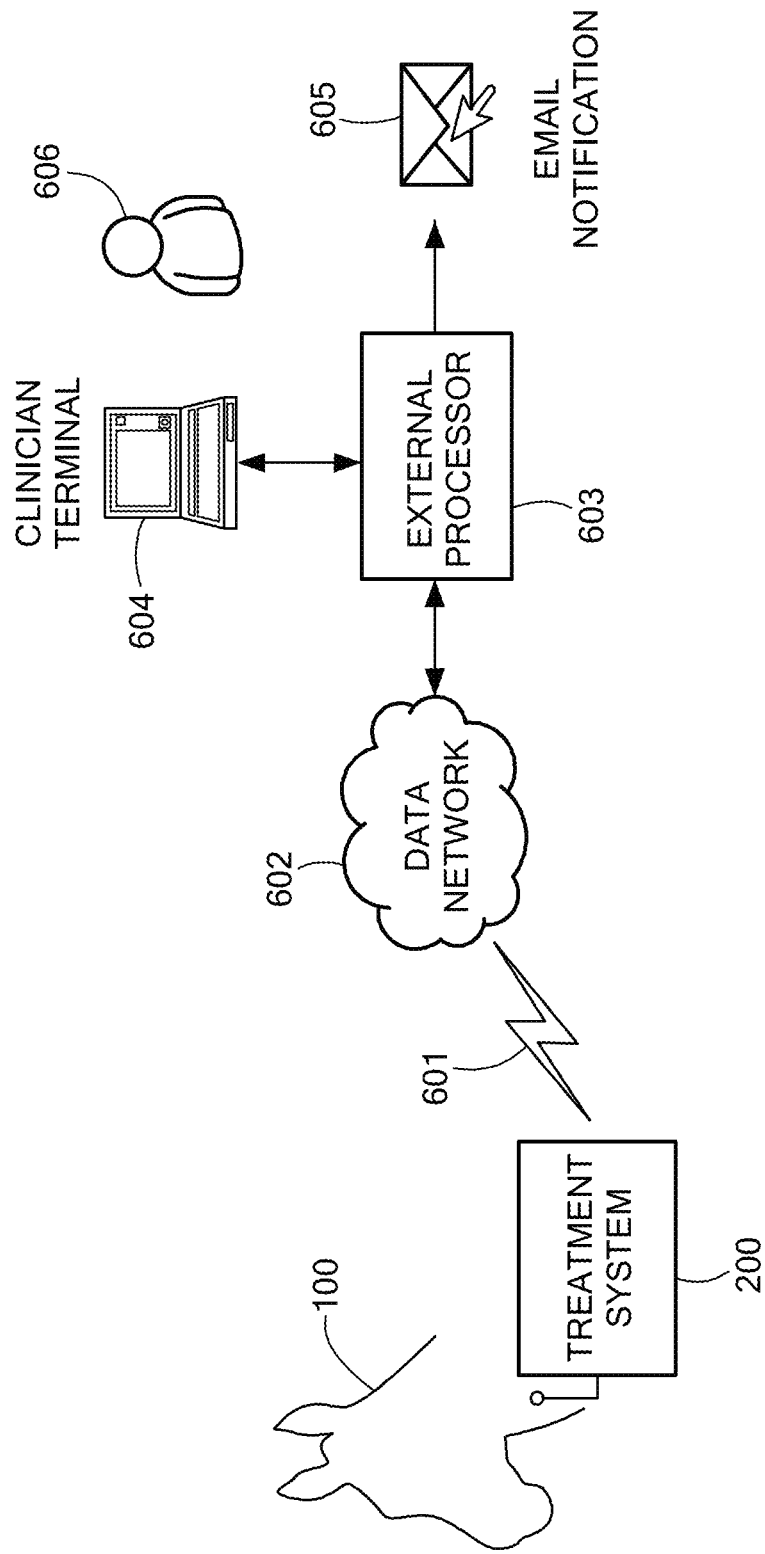
FIG. 6 illustrates various components for making parameter adjustments to an airway treatment.

In embodiments that include a sensor electrode 207, the pacemaker processor 201 and/or the stimulation module 204 may receive information from the sensor electrode 207 via wireless telemetry. The sensor electrode 207 may be an external component which is not implanted. In alternative embodiments, the sensor electrode 207 may be integrated within the housing of the stimulation module 204 and/or the pacemaker processor 201, or be coupled to one or both of them via one or more leads. FIG. 6 shows an embodiment in which an external processor 603 also may transmit information to the treatment system 200, such as adjustments to stimulation parameters to be applied by the stimulation module 204. The adjustments may be made based on the information received from the treatment system, for example, from the stimulation module 204 or the sensor electrode 207, or from a source external to the treatment system 200 such as a horse expert human user 606 via a clinician terminal 604 user interface with the external processor 603, or some combination thereof.

In one specific embodiment, the pacemaker processor 201 may record the received information, analyze the information, and adjust stimulation parameters based on the information, or some combination thereof. Alternatively, the pacemaker processor 201 may record information and transmit the information to the external processor 603 via a data network 602. In this case, the external processor 603 analyzes the information to generate adjustments to system characteristics such as stimulation parameters, and transmits the adjustments to the treatment system 200 for the pacemaker processor 201 for application to the stimulation module 204. One of skill in the art will also understand and appreciate that a separate processor responsible for analyzing the received information and proposing or instituting adjusted stimulation parameters could also be associated with the treatment system 200. As used herein, "associated with" refers to a structure that is either housed with or within a device, or attached to a device via a lead.

One or more of the clinician terminals 604 may be coupled to a data network 602 to receive or access notifications of system operations such as stimulation parameter adjustments which may be generated by the pacemaker processor 201 or the external processor 603. In one embodiment, a clinician terminal 604 can be used by a clinician user 606 to reject or approve stimulation parameter adjustments. In the case of approval, the treatment system 200 proceeds to have the pacemaker processor 201 make the adjustments to the stimulation parameters by downloading or inputting the adjustments to the implanted the stimulation module 204, e.g., as a new stimulation program, new parameters, or parameter adjustments. Alternatively, the clinician user 604 may require a clinical visit by the horse so that the clinician user 604 may supervise the parameter adjustments using the clinician terminal 604 or a separate user programmer device.

Data network 602 may take the form of a local area network, wide area network or global network such as the Internet. An external processor 603 may include a web server to generate web pages containing proposed parameter adjustments for viewing via the clinician terminal 604. In addition, the external processor 604 may include an email server for delivery of email notifications 605 of proposed parameter adjustments. The clinician terminal 604 may be any client device coupled to the data network 602, such as a personal computer, personal digital assistant, interactive television, mobile telephone, or the like. Using the clinician terminal 604, a clinician user 606 accesses web pages generated by the external processor 603 and receives email notifications 605 advising the clinician user 606 of new information or proposed parameter adjustments for the horse.

If the treatment system 200 itself (e.g., pacemaker processor 201) handles analysis of information and generation of proposed parameter adjustments, the adjustments and information still may be transmitted to the external processor 603 so that a clinician user 606 may review the information and adjustments via the clinician terminal 604. In this case, the pacemaker processor 201 provides intelligence for analysis and adjustment, but the external processor 603 supports reporting and approval, if necessary, prior to implementation of the adjustments. In other embodiments, the external processor 603 provides the intelligence for analysis and adjustment, as well as the reporting and approval mechanism. In this case, the external processor 603 serves as a conduit for collection and transmission of horse information and programming of the implanted stimulation module 204 to implement stimulation parameter adjustments. In some embodiments, approval by the clinician user 606 will only be necessary for certain stimulation parameter adjustments; for example, adjustments of a greater magnitude than a predetermined limit.

In some embodiments, stimulation parameter adjustments may be made automatically by the external processor 603, but in many circumstances, however, it will be desirable to obtain approval from the clinician user 606 prior to downloading or inputting stimulation parameter adjustments into the treatment system 200. For this reason, it is desirable that the external processor 603 supports the generation of email notifications 605 and web pages containing detailed reports so that the clinician user 606 has the information necessary to make a decision about stimulation parameter adjustment. The external processor 603 may manage information and parameter adjustment decisions for multiple horses as well as multiple clinicians. In each case, the external processor 603 and the treatment system 200 cooperate to provide adaptive adjustment of stimulation parameters applied by the stimulation module 604 for management of the disease.

The information obtained by the external processor 603 may be provided by the stimulation module 604, the sensor electrode 207, the horse 100, or some combination thereof. In the case of the stimulation module 204, the information may include operational information relating to the stimulation therapy delivered by the stimulation electrodes 205. Examples of operational information include battery status, charging status, lead impedance, parameter sets applied by the stimulation module 204, telemetry status, time since implant of the stimulation module 204, and information regarding the elapsed time since the stimulation parameters were adjusted. In some embodiments, the parameter sets can include details regarding the frequency, amplitude, and pulse width of stimulation, cycling parameters, identification of the stimulation electrodes 205 being used, and other similar parameters. Also, in some embodiments, the implanted stimulation module 204 may serve to receive information from the sensor electrode 207 and forward the information to the external processor 603. Alternatively, in other embodiments, the sensor electrode 207 may transmit information directly to the external processor 603.

One or more sensor electrodes 207 may provide a variety of information indicative of the level of efficacy achieved by the neurostimulation therapy delivered by the stimulation module 204. The information may be any information relating to the function of the vocal cords, or any other segment of the horse's airway tract, or any parameter inside the horse's body. For example, the sensor electrode 207 may monitor parameters such as pressure, contractile force, flow rate, flow pressure, airflow amount, and the like. Other examples of sensed information include flow velocity, temperature, impedance, pH, or chemical constituency. Any of such information may reveal the effect of the neurostimulation therapy on the physiological function of the horse 100. For example, if the sensor electrode 207 indicates excessive pressure, excessive contractile force, or involuntary flow (i.e., leakage) in response to a set of stimulation parameters, it may be desirable to dynamically adjust the stimulation parameters to reduce the pressure or contractile force, and thereby enhance efficacy.

In still other embodiments, one or more sensor electrodes 207 may be implanted within a horse 100 to sense a physiological state of the horse 100. For example, a sensor electrode 207 may be deployed to sense cardiac activity, respiratory activity, electromyographic activity, or the like, as an indication of horse activity level. Such activity level information, in conjunction with other information, may be useful in determining adjustments to stimulation parameters. Other types of sensor electrodes 207 also may detect a posture or activity level of the horse 100. For example, an accelerometer may detect an elevated activity level, e.g., during exercise, while other the sensors may detect whether the horse 100 is sitting, standing, or lying down. In addition, some of the information obtained by such sensor electrodes 207, such as respiration activity, may be analyzed to determine, e.g., whether the horse 100 is sleeping.

Information obtained from the horse 100 includes information entered into the external processor 603 via a clinician terminal 604 having a user interface such as a set of buttons, a keypad, a touch screen, or other input media. Like the information obtained from the sensor electrode 207, the information obtained from the horse 100 also may indicate a level of efficacy achieved by the neurostimulation therapy. Other information obtained from horse 100 may indicate a physiological state of the horse 100, such as an activity type (e.g., working, eating, sleeping), activity level (e.g., strenuous, moderate, or resting), or posture (standing, sitting, lying down). Input such as this can be relevant because the efficacy of particular stimulation parameters may vary as the physiological state of the horse 100 changes. Information regarding the comfort of the horse 100 may also be obtained. For example, discomfort can be noted and rated on a relative scale by a clinician user 606. In yet another embodiment, a clinician user 606 can input information regarding the overall subjective feeling of the horse 100 with respect to the stimulation therapy. This input could again be based on rating the overall feeling on a relative scale.

Also, in some embodiments, a clinician user 606 may be permitted to enter horse preferences, e.g., based on subjective sensations experience by the horse 100. For example, a clinician user 606 may enter information indicating that a stimulation level, e.g., amplitude, pulse width, or pulse rate, is unpleasant or even painful. In addition, a clinician user 606 may enter information for stimulation levels that seems to have no perceived efficacy from the horse's perspective. All of the information obtained by the external processor 603 or the treatment system 200 may be temporally correlated so that it is possible to evaluate the conditions experienced by a horse 100, e.g., at the time of a significant event.

The adaptation logic may take the form of a function or set of functions, expressed mathematically or in a lookup table, that weight various informational items with predetermined coefficients and sum the weighted items to produce a parameter adjustment. In one embodiment, the adaptation logic could be based at least in part on some combination of safety ranges (for example, determined by a manufacturer or the clinician user 604), efficacy of the stimulation, and battery life. In another embodiment, the adaptation logic includes weighting of all of the information received by the external processor 603 and/or the treatment system 200 (e.g. stimulation module 204, sensor electrode 207, etc.). In a further embodiment, the adaptation logic could also include weighting of other parameters input from the clinician user 606 either through initial programming of the external processor 603 and/or the treatment system 200 (e.g., pacemaker processor 201). In one embodiment, the safety ranges, whether determined by a manufacturer or the clinician user 606, set the limits of the parameter adjustment and/or are weighted most heavily by the adaptation logic.

The stimulation parameter adjustments may be expressed as an upward or downward change in one or more parameters such as amplitude, pulse width, or frequency. The stimulation parameter adjustments may be expressed as an absolute magnitude of adjustment or an incremental adjustment. In other words, the stimulation parameter adjustments may be applied in a single step in the amount specified by the output of the external processor 603. If the adaptation logic, upon analysis of the information, specifies an increase of 20 Hz in the frequency of the stimulation pulses applied by the stimulation module 204, then that 20 Hz increase is proposed as an instant adjustment to the stimulation parameters. In some cases, an absolute adjustment may be limited either by the manufacturer or by the clinician user 606 to a maximum adjustment to avoid instantaneous changes that cause abrupt discomfort for horse 100.

Alternatively, the adaptation logic may simply indicate that an increase is necessary, in which case a series of incremental increases are applied at periodic intervals until the adaptation logic no longer indicates the need for an increase. For example, frequency may be increased in 1 Hz increments for so long as the adaptation logic indicates the need for an increase. In this case, a hysteresis function may be built into the logic to avoid repeated up/down toggling of the stimulation parameters. The adjustments may be carried out at different intervals, such as seconds, minutes, hours, and even days, subject to the discretion of the clinician user 606. In addition to increases or decreases in parameters, the adaptation logic also may indicate that the efficacy is within an acceptable range, and provide an output indicating no need for adjustment.

In one embodiment, the external processor 603 may also determine and modify the frequency of analyzing and adjusting the stimulation parameters. For example, upon implantation and soon thereafter, more adjustment may be necessary or desirable to obtain the most beneficial stimulation settings. In one embodiment, the timing of when to analyze the stimulation parameters can be determined at least in part by analyzing the history of the stimulation parameters, and adjustment thereof. Alternatively, the timing of the adjustment analysis can be pre-determined by the clinician user 606, the manufacturer, or both. In yet another embodiment, the clinician user 606 treating the horse 100 can indicate, based on a subjective analysis of the efficacy of the current parameters, that the external processor 603 should analyze the stimulation parameters to determine if an adjustment is necessary.

In embodiments in which the external processor 603 or the treatment system 200 are permitted to directly and automatically adjust the stimulation parameters, the information may be analyzed on a periodic basis, e.g., at intervals on the order of seconds, minutes, hours, or days. In some embodiments, the external processor 603 and the treatment system 200 may apply different analysis modes. In a first mode, the information may be analyzed and adjustments made at relatively infrequent periodic intervals on the order of several hours or several days. In a second mode, the external processor 603 or the treatment system 200 may operate in a more intensive analysis and adjustment mode in which information is evaluated and parameters are adjusted very frequently until a desired level of efficacy is achieved. This second, more intensive mode may continue until the efficacy level is driven into an acceptable range. The intensive mode may be entered when analysis in the first infrequent mode reveals efficacy levels that require stimulation parameter adjustments. Again, the adjustments made to the stimulation parameters in either mode may be performed automatically or subject to approval by the clinician user 606.

In one embodiment, the external processor 603 can, without further input or authorization from any other source, input and utilize the new stimulation parameters. As discussed above, another embodiment requires approval by the clinician user 606 through the external processor 603 before the new simulation parameters can be instituted and utilized. In yet another embodiment, the external processor 603 can send the new stimulation parameters to the clinician terminal 604 for review and/or approval by the clinician user 606 treating the horse 100. This embodiment could allow the clinician user 606 treating the horse 100 to subjectively compare the efficacy of the two stimulation parameters and pick which settings they prefer. Furthermore, a number of previous stimulation parameters could be stored in memory to allow the clinician user 606 treating the horse 100 to pick from them, or designate some as particularly efficacious, particularly undesirable, or particularly efficacious for one or more activity levels or types (i.e. a particularly desirable setting for exercise).

The sensor module 208 and/or the sensor electrode 207 may be chronically implanted within a horse 100 for use over an extended period of time. In this case, the sensor module 208 carries sufficient battery resources, a rechargeable battery, or an inductive power interface that permits extended operation. The sensor module 208 and/or sensor electrode 207 may be implanted by minimally invasive, endoscopic techniques for an extended period of time or a limited period of time to capture information useful in analyzing and adjusting the stimulation parameters. In other words, the sensor module 208 and/or sensor electrode 207 may be chronically implanted to support ongoing parameter adjustments over an extended course of therapy spanning several months or years, or purposefully implanted for a short period of time to support a one-time parameter adjustment or a small number of adjustments over a relatively short period of time, such as several hours, days, or weeks.

In some embodiments, the sensor module 208 transmits sensed information continuously or periodically to the stimulation module 204 or the external processor 603. In this case, the sensor module 208 monitors physiological conditions continuously or periodically. Alternatively, the stimulation module 204 or the external processor 603 may trigger activation of the sensor module 208 to capture information at desired intervals. In some cases, triggered activation may occur when the clinician user 606 treating the horse 100 enters information into the external processor 603. Triggered activation of the sensor module 208 may be useful in conserving battery life, if applicable, of the sensor module 208 or the stimulation module 204. In each case, multiple sensor electrodes 207 may be provided and dedicated to different parameters or different locations within the horse 100.

Rather than immediately transmitting the information to the stimulation module 204 or the external processor 603, the sensor module 208 may initially store the information internally for subsequent wireless transmission 601. Hence, in some embodiments, the information may be stored within the sensor module 208, and later communicated to the stimulation module 204 or the external processor 603. In this case, the stimulation module 204 or the external processor 603 may interrogate the sensor module 208 to obtain the stored information for analysis and possible adjustment of stimulation parameters. As a further alternative, triggered activation may be applied by the clinician user 604 treating the horse 100 in the form of a magnet swiped in proximity to the sensor electrode 207, in which case the sensor monitor 208 will include appropriate sensing circuitry to detect the magnet use.

An embodiment may include a monitoring server, a web server, an email server, a programming server, a network link, a horse database, or some combination thereof. The horse database may store information for multiple horses 100 in an organized form that permits ready retrieval of information for analysis, reporting, and historical archival. The web server generates web pages that contain information obtained for one or more horses 100, including information obtained from the external processors 603. The information may be presented in a variety of formats and levels of detail. Using a clinician terminal 604 equipped with a web browser, a clinician user 606 can view information contained in horse database by accessing the web server. The web server also may be configured to execute database access commands to retrieve desired information. In some embodiments, the information may be organized using a hierarchy of XML tags. The information contained in the web pages also may include proposed stimulation parameter adjustments. The stimulation parameter adjustments may be generated by the external processor 603 or the treatment system 200. A clinician user 606 may approve the stimulation parameter adjustments by clicking on a button within the web page. Upon receipt of clinician approval, the treatment system 200 may then proceed to interact with the external processor 603 to implement the stimulation parameter changes in the stimulation module 204. The web page generated by the web server also may offer the clinician user 606 the opportunity to modify the proposed stimulation parameter adjustments before approval, e.g., using boxes, drop down menus, slider bars, radio buttons, or the like. In this case, the treatment system 200 implements the stimulation parameter adjustments as modified by the clinician user 606.

An email server provides email notifications 605 to the clinician terminal 604, if desired. The email notifications 605 may report newly acquired information for a particular horse 100, or proposed stimulation parameter adjustments for the horse 100. The email notifications 605 may include links to web pages for approval or modification of the proposed stimulation parameter adjustments. Alternatively, in some embodiments, the clinician user 606 may approve stimulation parameter adjustments by replying to the email notification 605. In either case, the proposed stimulation parameter adjustments are not implemented until approval is received. In other embodiments, however, it is conceivable that stimulation parameter adjustments may be fully automatic, and not require approval by the clinician user 606, particularly if stimulation parameter adjustments are subject to pre-programmed limits within the external processor 603 or the stimulation module 204.

Some embodiments may be used to support clinical research. For example, the external processor 603, the treatment system 200 and the clinician terminals 604 may permit clinical user 606 researchers to access information obtained from implanted stimulation modules 204 for purposes of research, and not necessarily for adjustment of stimulation parameters. Rather, clinician user 606 researchers may access the information obtained from the external processor 603 and the treatment system 200 via clinician terminals 604 to gather information in support of short or long range research for formulation of improved or enhanced therapies. In some embodiments, adaptation logic may be configured to apply particular algorithms such as genetic algorithms, Bayesian classification, neural networks, or decision trees. In those cases, adaptation logic may be formulated to implement algorithms similar to those described in U.S. patent application Ser. No. 10/767,674; U.S. patent application Ser. No. 10/767,922; U.S. patent application Ser. No. 10/767,545; and U.S. patent application Ser. No. 10/767,692, each of which is incorporated herein by reference.

Treatment Verification Monitoring

Related to the foregoing, there also is a need in horse racing to follow the rules of the governing agencies such that a treatment system 200 or treatment method would not create an unfair advantage, disadvantage, or erroneous response. The therapeutic goal is to restore function without supra-maximal or supra-physiological advantage. Accordingly, embodiments may allow various safeguards to not influencing wagering. A logging system may document use and frequency of the stimulation protocol. For example, as shown in FIG. 2, a verification monitor 209 and corresponding record log 210 may act as a logging system which allows an equipment person in the paddocks or the competition arena to readily assess that the treatment system 200 is active and functioning appropriately. The logging system should be easy to monitor under the conditions of competition.

Embodiments also include a treatment system 200 that does not influence other biological functions of the horse 100 apart from the airway disorder that is being treated. Specifically, it is undesirable that the treatment system 200 would cause any other effects that could stimulate or impair the athletic performance of the horse 100. This is partly satisfied by the design of the treatment system 200 discussed herein. However, a method of ensuring that there are no extraneous effects is to test the treatment system 200 and measure physiological parameters including but not limited to contralateral vocal cord abduction, heart rate blood pressure, respiratory rate, or the multiple other physiological parameters mentioned herein or known in the art.

And embodiments include methods to satisfy the spirit and rules of agencies governing equine sporting events, including monitoring devices and methods such as a verification monitor 209 and/or record log 210 which allow calibration by an attending veterinarian only, where the stimulation parameters are fixed and can only be adjusted by race track personnel or attending veterinarians. In addition or alternatively, the athletic governing authority can monitor the effect of the treatment system 200 before, during, or after an athletic performance. The monitoring authority may want to know that the treatment system 200 was on and delivering proper electrical stimulation, that the treatment system 200 senses that the vocal fold was abducted, and that air was passing unrestricted through the larynx during inspiration. Along these lines, a variety of physiological parameters may be sensed and stored (data logging in the record log 210) or transmitted outside the horse 100. Examples of data logging of such information include without limitation stimulation parameters; nerve action potentials; microphone, acoustic, or subglottic pressure monitoring airways; tracheal pressure; and vocal fold abduction reflected by electroglottography (EGG—laryngeal impedance to hi-frequency electrical fields). In addition, light produced by a source located on one side of the larynx may be sensed by a light the sensor located on the other side.

In one specific embodiment, an external signal can be produced when the treatment system 200 is working; for example, a light on an outer component that is active and visible with proper stimulation. Another example is a radio signal that can be sensed by receivers at a distance. In another embodiment, a separate lead and electrode stimulate another muscle of the horse 100 such that its effects were clearly visible, e.g., stimulation of the muscle that moves the auricle so that the auricle tilts or rotates when the treatment system 200 is active.

The sensor electrodes 207 and sensor module 208 may sense electrical stimulation, electrical biopotentials from nerve or muscle activity evoked by stimulation, mechanically sense vocal fold abduction, or changes in airflow related to vocal fold position. Proper stimulation abducts the vocal fold and allows maximum airflow, which can be monitored by the sound of the air moving through the airway, subglottic pressure, or temperature. Vocal fold movement can be sensed by vocal fold displacement as measured by any of various specific means such as strain gauges in laryngeal tissue, the amount of light passing across the glottis, changes in tissue impedance across the larynx, or direct visualization of the vocal folds with an in-dwelling video camera. Interference with inspiratory airflow may be sensed by pressure sensors in the subglottis or trachea, or outside the trachea but within the thorax. Such pressure sensors would show abnormally high negative pressure as resistance to airflow increased due to a medially positioned vocal fold. Inefficient respiration during exercise would rapidly be reflected in systemic physiologic signals: blood oxygen decreasing and $CO_2$ increasing.

Embodiments of the present invention include endoscopically controlled, minimally invasive positioning of an electrode or electrodes, which reduces the surgical risks and at the same time allows an adjustment of stimulation to the individual deficit of the patient in vocalization, breathing, and/or swallowing by stimulating opening, closing, and/or elevation of the larynx. Some embodiments may allow more than one electrode to be inserted (e.g., bilaterally, or separate electrodes for opening and closing, or larynx elevation). "Pull through" techniques may call for reinforcement of the electrode structure to accommodate the resulting traction stress. One particularly gently technique is to push in the electrode under endoscopic view. Endoscopic control and intraoperative stimulation assist in obtaining an optimal positioning of the electrodes (as in some of the examples described above). Bilateral electrode placements further offer the advantage of improved three-dimensional electric dipole vectors for optimal stimulation which may further improve flexibility. Bilateral separately controlled electrodes may also provide greater safety in case of device failure. For example, if one side fails, the other side may (partially) compensate until the patient receives clinical help.

Embodiments of the present invention also are directed to a minimally invasive, two-stage implantation procedure. First, an electrode is inserted. Then, a test stimulation session may be conducted over time, e.g., over several days, to show efficiency of the system. When efficiency is verified, a stimulator may also be implanted and the electrode may be retracted out of the body without a complicated surgery.

Embodiments include the implantation of a stimulation electrode of the larynx using minimal invasive endoscopic techniques. For example, one embodiment uses straight tubular electrodes that may be inserted in a "pull back" procedure on an implanted thread that the electrode is attached to.

Embodiments of the present invention also permit a minimally invasive, two-stage implantation procedure. First, the electrode may be inserted as disclosed above, but the stimulator itself is not implanted during the same surgery, but is left outside the body. A test stimulation session may then be performed over time (minutes, hours or several days), and if this test stimulation session shows efficiency, the stimulator may be sterilized and the housing of the pacer may be implanted via the small subcutaneous tunnel into the subcutaneous pocket. In case the stimulation system is not efficient enough, the electrode may be retracted out of the body without a complicated surgery simply by pulling the electrode back so its tip leaves the skin.

Surgical tools may be traditional surgical tools for a thyrotomy approach include known tools from veterinary and human surgical theaters, and/or new tools which may incorporate, for example, electrodes that are inflated for insertion and then deflated when in final position by another part of the tool or by a kind of memory effect. These tools may be independent tools or part of an endoscopic system. Electrodes may be anchored, for example, by sutures, glue, or attached anchors which do not limit insertion but resist unwanted migration.

Embodiments of the present invention allow an FES device to survive the harsh environment within the neck of a horse and work reliably for months. In still further embodiments, an implanted device can signal when it is working properly so that it can be monitored by regulatory officials—and this can be confirmed before, during, and after an athletic event by other methods and devices that are embodiments of this invention.

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of using an airway treatment system for treating a dorsal displacement disorder in a horse, the method comprising:
    detecting an elevated activity level of the horse sufficient to cause the dorsal displacement disorder;
    generating a treatment signal configured to treat the dorsal displacement disorder based on the detected elevated activity level, using a pacemaker processor, to strengthen one or more muscles involved in displacing a laryngeal anatomical structure relative to an airway of the horse; and
    using one or more stimulation electrodes, configured to interface with tissue of the horse, to deliver the treatment signal to the tissue of the horse to maintain an unobstructed airway.

2. The method of claim 1, wherein the displacing of the laryngeal anatomical structure relative to the airway includes a reduced distance between larynx and basihyoid bone.

3. The method of claim 1, wherein the displacing of the laryngeal anatomical structure relative to the airway includes a reduced distance between larynx and chin.

4. The method of claim 1, wherein the displacing of the laryngeal anatomical structure relative to the airway includes a reduced distance between larynx and basihyoid bone and chin simultaneously.

5. The method of claim 1, wherein the displacing of the laryngeal anatomical structure relative to the airway includes a reduced distance between basihyoid and larynx and ventral aspect of the petrous temporal/basisphenoid bone.

6. The method of claim 1, further comprising recording the elevated activity level using the pacemaker processor.

7. The method of claim 1, further comprising:
    monitoring the elevated activity level using the pacemaker processor; and
    adjusting the treatment signal based on the monitored elevated activity level.

8. The method of claim 1, further comprising:
    monitoring the treatment signals using the pacemaker processor; and
    adjusting the treatment signal based on the monitored treatment signals.

9. The method of claim 1, wherein the one or more stimulation electrodes include a cuff electrode, a multipolar cuff electrode, a tripolar cuff electrode, a flat nerve electrode, an epineural electrode, a shaft electrode, a longitudinal intrafascicular electrode, a thin wire electrode, a micro-machined electrode, a sieve electrode, or combinations thereof.

10. The method of claim 1, wherein the one or more stimulation electrodes are configured to cause stimulation to a specific area of the tissue of the horse by differential activation.

11. The method of claim 1, wherein the treatment signal is delivered continuously over a period of hours until the system is turned off.

12. The method of claim 1, wherein the treatment signal is further based on air flow characteristics of the airway tract of the horse, contractile characteristics of the airway tissue of the horse, electrical characteristics of a portion of the body of the horse, temperature of a portion of the body of the horse, pH of a portion of the body of the horse, chemical constituency of a portion of the body of the horse, physiological state of the horse or combinations thereof.

13. The method of claim 1, further comprising monitoring operation of the pacemaker processor using a treatment verification monitor.

14. The method of claim 1, wherein the tissue of the horse is selected from the group consisting of geniohyoid muscle tissue, mylohyoid muscle tissue, nerve tissue to the palatoglossus muscle, nerve tissue to the palatopharyngeus muscle, thyrohyoid muscle tissue, nerve tissue to the thyrohyoid muscle, and combinations thereof.

15. The method of claim 1, wherein the elevated activity level of the horse sufficient to cause the dorsal displacement disorder is detected with one or more treatment sensors.

16. The method of claim 15, wherein the one or more treatment sensors includes an accelerometer, an electromyogram, an electronystagmograph, an electroglottograph, an electroencephalograph, a biopotential sensor, an ultrasound sensor, a hall sensor, a microphone, a pressure sensor, a strain transducer, a mechanical deformation sensor, a motion sensor, or combinations thereof.

17. A method of using an airway treatment system for treating a dorsal displacement disorder in a horse, the method comprising:
    generating a treatment signal configured to treat the dorsal displacement disorder, using a pacemaker processor, to strengthen one or more muscles involved in displacing a laryngeal anatomical structure relative to an airway of the horse; and
    using one or more stimulation electrodes, configured to interface with tissue of the horse, to deliver the treatment signal to the tissue of the horse to maintain an unobstructed airway.

18. The method of claim 17, wherein the treatment signal is delivered continuously over a period of hours.

* * * * *